United States Patent [19]

Hodges et al.

[11] Patent Number: 5,468,484

[45] Date of Patent: Nov. 21, 1995

[54] METHOD OF PREVENTION OF PSEUDOMONAS INFECTION

[75] Inventors: Robert S. Hodges, Edmonton; Randall T. Irvin, Sherwood Park; William Paranchych, Edmonton; Pamela A. Sokol; Donald E. Woods, both of Calgary, all of Canada

[73] Assignee: S.P.I. Synthetic Peptides Incorporated, Edmonton, Canada

[21] Appl. No.: 84,739

[22] Filed: Jun. 28, 1993

Related U.S. Application Data

[63] Continuation-in-part of Ser. No. 721,759, Jun. 25, 1991, Pat. No. 5,223,604.

[51] Int. Cl.$^6$ ............... A61K 39/395; A61K 39/40; C07K 15/28; C12P 21/08
[52] U.S. Cl. ............... 424/141.1; 424/134.1; 424/139.1; 424/150.1; 424/169.1; 424/170.1; 424/152.1; 530/300; 530/327; 530/387.1; 530/387.9; 530/388.1; 530/388.2; 530/388.4
[58] Field of Search ............... 424/85.8, 134, 424/139.1, 141.1, 150.1, 164.1, 170.1; 530/387.1, 387.9, 388.1, 300, 327

[56] References Cited

PUBLICATIONS

Pavlovskis et al, Medical Microbiology 1:97–128, 1982.
Coburn, Curr Top Microbiol & Immunology 175; 133–141, 1992.
Holder, Serodiagnosis & Immuno Therapy 2: 7–16 1988.
Nicas et al, The Journal of Infetious Diseases 152:716–721, 1985. The role of Exoenzymes.
Lingwood et al, Biochemical & Biophysical Res & Comm 175: 1076–1081, 1991 (Mar.) Glycolipid Receptor Binding Specificity of Exoenzyme S from Pseudomonas Aeruginosa.
Woods et al. Evr. J. Clin. Microbiol 4:163–169, 1985.
Infections With Pseudomonas Aeruginosa.
Ramphal et al, Infection and Immunity 58:600–603 1987.
Baker et al., Infection and Immunity 58:2361–2366 1990, Glycosphingulipid Receptors for Peudomonas Aeruginosu.

*Primary Examiner*—Hazel F. Sidberry
*Attorney, Agent, or Firm*—Peter J. Dehlinger; Carol A. Stratford

[57] ABSTRACT

The invention described includes methods and compositions useful in preventing infection by *Pseudomonas aeruginosa* and related organisms. Diclosed is a peptide having the sequence corresponding to an antigenic site in the protein exoenzyme S which is antigenically similar to a C-terminal portion of the *Pseudomonas aeruginosa* pilin protein. The peptide is cross-reactive with surface peptides present in certain bacterial and fungal microorganisms, and is effective in inhibiting binding of such organisms to target epithelial cells. The peptide may also be employed in a vaccine composition, for producing immunity against *Pseudomonas aeruginosa* as well as against such cross-reactive microorganisms.

3 Claims, 7 Drawing Sheets

```
                    Glu    Gln
                  (P,A)(M,K)      Phe
          Asp(E)
         Gln(V)                   (R,T)Ile
        Asp(T)                          Pro
       Ser(T)                        (N)Lys
      Thr(K,A)                          Gly
       Cys ———————— S ———————— S ———————— Cys
```

Fig. 1A

```
                        ↓
                    Ala     Thr
                  (E,P,A)(Q,M,K)
              — (D,E)              (F) Gly
              — (Q,V)              (I,R,T) —
          ⟶ Thr (D,T)                   (P) Pro ⟵
          ⟶ Thr (S,T)                   (K,N) Asn ⟵
          ⟶ Ala (T,K,A)                    (G) Gly ⟵
                                           (−) Ser
          ⟶ Cys ———————— S ———————— S ———————— Cys ⟵
```

```
PAK:   K C T S D Q D E Q F I P K G C S K
PAO:   A C K S T Q D P M F T P K G C D N
P1:    N C K I T K T P T A W K P N Y A P A N C P K
KB7:   S C A T T V D A K F R P N G C T D
K122:  A C T S N A D N K Y L P K T C Q T
CD4:   T C T S T Q E E M F I P K G C N K
GA:    T C G I T G S P T D W K T N W A P A N C P K
492C:  T C G I T G S P T N W K A N Y A P A N C P K
```

Fig. 8

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: ExoS DNA Sequence, Pg. 12

( x i ) SEQUENCE DESCRIPTION: SEQ ID NO:1:

TGCCGCACTA    CCGCTACTGG    CCCGAATGGC    AGTTGC                    3 6

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: both ( i i ) MOLECULE TYPE: peptide ( i i i ) HYPOTHETICAL: NO ( v i ) ORIGINAL SOURCE:
        ( C ) INDIVIDUAL ISOLATE: ExoS Derived Peptide, Fig. 1B ( x i ) SEQUENCE DESCRIPTION: SEQ ID NO:2:

Cys  Ala  Thr  Thr  Ala  Thr  Gly  Pro  Asn  Gly  Ser  Cys
    1                   5                            1 0

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( D ) TOPOLOGY: both ( i i ) MOLECULE TYPE: peptide ( i i i ) HYPOTHETICAL: NO ( v i ) ORIGINAL SOURCE:
        ( C ) INDIVIDUAL ISOLATE: Pilin Peptide, Fig. 1A ( x i ) SEQUENCE DESCRIPTION: SEQ ID NO:3:

Cys  Thr  Ser  Asp  Gln  Asp  Glu  Gln  Phe  Ile  Pro  Lys  Gly  Cys
    1                   5                            1 0

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide (i i i) HYPOTHETICAL: NO (v i) ORIGINAL SOURCE:
(C) INDIVIDUAL ISOLATE: Peptide 1KO43, Pg. 25

(x i) SEQUENCE DESCRIPTION: SEQ ID NO:4:

Asp Glu Gln Phe Ile Pro Lys
1               5

(2) INFORMATION FOR SEQ ID NO:5:

(i) SEQUENCE CHARACTERISTICS:
(A) LENGTH: 17 amino acids
(B) TYPE: amino acid
(D) TOPOLOGY: both (i i) MOLECULE TYPE: peptide (i i i) HYPOTHETICAL: NO (v i) ORIGINAL SOURCE:
(C) INDIVIDUAL ISOLATE: PAK, Fig. 8

(x i) SEQUENCE DESCRIPTION: SEQ ID NO:5:

Lys Cys Thr Ser Asp Gln Asp Glu Gln Phe Ile Pro Lys Gly Cys Ser
1               5                   10                  15

Lys (2) INFORMATION FOR SEQ ID NO:6:

(i) SEQUENCE CHARACTERISTICS:
(A) LENGTH: 17 amino acids
(B) TYPE: amino acid
(D) TOPOLOGY: both (i i) MOLECULE TYPE: peptide (i i i) HYPOTHETICAL: NO (v i) ORIGINAL SOURCE:
(C) INDIVIDUAL ISOLATE: PAO, Fig. 8

(x i) SEQUENCE DESCRIPTION: SEQ ID NO:6:

Ala Cys Lys Ser Thr Gln Asp Pro Met Phe Thr Pro Lys Gly Cys Asp
1               5                   10                  15

Asn (2) INFORMATION FOR SEQ ID NO:7:

(i) SEQUENCE CHARACTERISTICS:
(A) LENGTH: 22 amino acids
(B) TYPE: amino acid
(D) TOPOLOGY: both (i i) MOLECULE TYPE: peptide (i i i) HYPOTHETICAL: NO (v i) ORIGINAL SOURCE:
(C) INDIVIDUAL ISOLATE: P1, Fig. 8

(x i) SEQUENCE DESCRIPTION: SEQ ID NO:7:

Asn Cys Lys Ile Thr Lys Thr Pro Thr Ala Trp Lys Pro Asn Tyr Ala
1               5                   10                  15

Pro Ala Asn Cys Pro Lys
            20

(2) INFORMATION FOR SEQ ID NO:8:

( i ) SEQUENCE CHARACTERISTICS:
    ( A ) LENGTH: 17 amino acids
    ( B ) TYPE: amino acid
    ( D ) TOPOLOGY: both ( i i ) MOLECULE TYPE: peptide ( i i i ) HYPOTHETICAL: NO ( v i ) ORIGINAL SOURCE:
    ( C ) INDIVIDUAL ISOLATE: KB7, Fig. 8

( x i ) SEQUENCE DESCRIPTION: SEQ ID NO:8:

Ser Cys Ala Thr Thr Val Asp Ala Lys Phe Arg Pro Asn Gly Cys Thr
1               5                   10                  15

Asp ( 2 ) INFORMATION FOR SEQ ID NO:9:

( i ) SEQUENCE CHARACTERISTICS:
    ( A ) LENGTH: 17 amino acids
    ( B ) TYPE: amino acid
    ( D ) TOPOLOGY: both ( i i ) MOLECULE TYPE: peptide ( i i i ) HYPOTHETICAL: NO ( v i ) ORIGINAL SOURCE:
    ( C ) INDIVIDUAL ISOLATE: K122, Fig. 8

( x i ) SEQUENCE DESCRIPTION: SEQ ID NO:9:

Ala Cys Thr Ser Asn Ala Asp Asn Lys Tyr Leu Pro Lys Thr Cys Gln
1               5                   10                  15

Thr ( 2 ) INFORMATION FOR SEQ ID NO:10:

( i ) SEQUENCE CHARACTERISTICS:
    ( A ) LENGTH: 17 amino acids
    ( B ) TYPE: amino acid
    ( D ) TOPOLOGY: both ( i i ) MOLECULE TYPE: peptide ( i i i ) HYPOTHETICAL: NO ( v i ) ORIGINAL SOURCE:
    ( C ) INDIVIDUAL ISOLATE: CD4, Fig. 8

( x i ) SEQUENCE DESCRIPTION: SEQ ID NO:10:

Thr Cys Thr Ser Thr Gln Glu Glu Met Phe Ile Pro Lys Gly Cys Asn
1               5                   10                  15

Lys ( 2 ) INFORMATION FOR SEQ ID NO:11:

( i ) SEQUENCE CHARACTERISTICS:
    ( A ) LENGTH: 22 amino acids
    ( B ) TYPE: amino acid
    ( D ) TOPOLOGY: both ( i i ) MOLECULE TYPE: peptide ( i i i ) HYPOTHETICAL: NO ( v i ) ORIGINAL SOURCE:
    ( C ) INDIVIDUAL ISOLATE: GA, Fig. 8

-continued (xi) SEQUENCE DESCRIPTION: SEQ ID NO:11:

Thr Cys Gly Ile Thr Gly Ser Pro Thr Asp Trp Lys Thr Asn Trp Ala
1               5                   10                  15

Pro Ala Asn Cys Pro Lys
                20

(2) INFORMATION FOR SEQ ID NO:12:

(i) SEQUENCE CHARACTERISTICS:
      (A) LENGTH: 22 amino acids
      (B) TYPE: amino acid
      (D) TOPOLOGY: both (ii) MOLECULE TYPE: peptide (iii) HYPOTHETICAL: NO (vi) ORIGINAL SOURCE:
      (C) INDIVIDUAL ISOLATE: 492c, Fig. 8

(xi) SEQUENCE DESCRIPTION: SEQ ID NO:12:

Thr Cys Gly Ile Thr Gly Ser Pro Thr Asn Trp Lys Ala Asn Tyr Ala
1               5                   10                  15

Pro Ala Asn Cys Pro Lys
                20

METHOD OF PREVENTION OF PSEUDOMONAS INFECTION

This application is a continuation-in-part of U.S. patent application U.S. Ser. No. 721,759, filed Jun. 25, 1991, now U.S. Pat. No. 5,223,604.

FIELD OF THE INVENTION

The present invention relates to Pseudomonas-derived polypeptide antigens, and to antibodies immunoreactive against the antigens.

REFERENCES

Adams, M. H., "Methods of study of bacterial viruses" in *Bacteriophages* (M. H. Adams, Ed.), Interscience Publishers, Inc., New York, pp. 443–452 (1959).

Ausubel, F. M., et al., in *Current Protocols in Molecular Biology*, John Wiley & Sons, Inc., Media, Pa. (1990).

Baker, N., *Abstr. Annu. Meet. Am. Soc. Microbiol.*, B-224:68 (1989).

Baker, N., et al., *Infect. Immun.* 58:2361–2366 (1990).

Beachy, E., *J. Infect. Disease* 413:325 (1981).

Bryan, C. S., et al., *Am. Rev. Respir. Dis.* 129:668 (1984).

Carr, B., et al., *Gerontology* 35:127 (1989).

Coburn, J., et al., *J. Biol. Chem.* 264:9004 (1989).

Dale, R. K., et al., *Plasmid* 13:31 (1985).

Devereux, J., et al., *Nuc. Acids Res.* 12:387 (1984).

Devlin, J. J., et al., *Science* 249:404 (1990).

Doig, P., et al., *Infect. Immunol.* 56:1641 (1988).

Doig, P., et al., *Can J. Microbiol.* 35:1141 (1989).

Doig, P., et al., *Infect. Immunol.* 58:124 (1990).

Farmer, J. J., III., *Hosp. Pract.* 10:63 (1976).

Franklin, A. L., et al., *Infect. Immunol.* 55:1523 (1987).

Geyson, H. M., et al., in "Synthetic Peptides as Antigens" in *Ciba Foundation Symposium* 119:131 (1986).

Godfrey, A. J., et al., *Antimicrob. Agents Chemother.* 30:802 (1986).

Hansson, G. C., et al., *Biochem. Biophys. Acta* 750:214 (1983).

Hazlett, L. D., et al., *Infect. Immunol.* 51:687 (1986).

Irvin, R. T., et al., *Can. J. Microbiol.* 31:268 (1985).

Irvin, R. T., et al., *Infect. Immunol.* 57:3720 (1989).

Irvin, R. T., et al., *Microb. Ecol. Health Dis.* 3:39 (1990).

Komiyama, K., et al., *Infect. Immunol.* 55:2364.

Krivan, H. C., et al., *Arch. Biochem. Biophys.* 26:493 (1988a).

Krivan, H. C., et al., *Proc. Natl. Acad. Sci. USA* 85:6157 (1988b).

Kulczyki, L. L., et al., *J. Am. Med. Assoc.* 240:30 (1978).

Laraya-Causey, L. R., et al., *J. Pediatr.* 89:23 (1976).

Lee, K. K., et al., *Infect. Immunol.* 57:520 (1989).

Lee, K. K., et al., *Infect. Immunol.* 58:2727 (1990).

Leprat, R., et al., *Ann. Microbiol.* (Paris) 131B:210 (1980).

Lund, B., et al., *Proc. Natl. Acad. Sci. USA* 84:5898 (1987).

Marrs, C. F., et al., *Am. J. Med.* 88(Suppl. 5A): 36S (1990).

McBride, L. J., et al., *Clin. Chem.* 35:2196 (1989).

McEachran, D. W., et al., *Can. J. Microbiol.* 31:563 (1985).

Mcgachran, D. W., et al., *J. Microbiol. Meth.* 5:99 (1986).

Morrison, S. L., et al., *Proc. Natl. Acad. Sci. USA* 81:6851 (1984).

Nieto, A., et al., *Mol. Immunol.* 21:537 (1984).

Paruchuri, D. K., et al., *Proc. Natl. Acad. Sci. USA* 87:333 (1990).

Pasloske, B. L., et al., *J. Bacteriol.* 170:3738 (1988).

Paranchych, W., et al., *Can. J. Microbiol.* 25:1175 (1979).

Paranchych, W., et al., *Advan. Microbiol. Phys.* 29:53 (1988).

Rabbitts, T. H., et al., *Nucleic Acids Res.* 9:4509 (1981).

Ramphal, R., et al., *Infect. Immunol.* 55:600 (1987).

Sanger, et al., *Proc. Natl. Acad. Sci. USA* 74:5463 (1977).

Sato, H., et al., *Infect. Immunol.* 55:1774 (1987).

Sastry, L., et al., *Can. J. Cell Biol.* 63:284 (1985).

Sastry, L., et al., *Proc. Natl. Acad. Sci. USA* 86:5728 (1989).

Scott, J. K., et al., *Science* 249:386 (1990).

Singh, A., et al., *Infect. Immunol.* 58:1301 (1990).

Sokol, P. A., et al., *Microbial Pathogenesis* 8:243 (1990).

Staddon, W., et al., *Can. J. Microbiol.* 36:336 (1990).

Stromberg, N., et al., *J. Biol. Chem.* 265:11252 (1990).

Tabor, S., et al., *Proc. Natl. Acad. Sci. USA* 84:4767 (1987).

Todd, T., et al., *Am. Rev. Respir. Dis.* 140:1585 (1989).

Towbin, M., et al., *Proc. Natl. Acad. Sci. USA* 76:4350 (1979).

Tsai, C., et al., *Anal. Biochem.* 119:115 (1982).

U.S. patent application Ser. No. 07/638,492.

U.S. patent application Ser. No. 07/344,565.

Woods, D. E., et al., *Infect. Immunol.* 29:1146 (1980).

Woods, D. E., et al., *Eur. J. Clin. Microbiol.* 4:163 (1985).

Woods, D. E., et al., *Infect. Immunol.* 55:579 (1987).

Woods, D. E., et al., *Antibiot. Chemother.* 42:27 (1989).

Worobec, E. A., et al., *J. Biol. Chem.* 260:938 (1985).

zuPutlitz, J., et al., *Bio/Technology* 8:651 (1990).

BACKGROUND OF THE INVENTION

During the past two decades, *Pseudomonas aeruginosa* has been recognized as a pathogen which causes between 10% and 20% of infections in most hospitals. Pseudomonas infection is especially prevalent among patients with burn wounds, cystic fibrosis, acute leukemia, organ transplants, and intravenous-drug addition. *P. aeruginosa* is a common nosocomial contaminant, and epidemics have been traced to many items in the hospital environment. Patients who are hospitalized for extended periods are frequently affected by this organisms and are at increased risk of developing infection. The most serious infections include malignant-external otitis, endophthalmitis, endoconditis, meningitis, pneumonia, and septicemia. The likelihood of recovery from Pseudomonas infection is related to the severity of the patient's underlying disease process. The reported mortality for *P. aeruginosa* pneumonia is as high as 50–80%. Even with the development of newer antibiotics, resistance remains a problem necessitating combined antibiotic treatment for severe *P. aeruginosa* infections.

Various therapies for the management of severe *P. aerugi-*

*nosa* infections have been evaluated for many years, with particular attention focused on virulence factors. As with most bacterial pathogens, virulence of *P. aeruginosa* is multifactorial and is the product of many interacting variables, involving both the bacterium and the host. Evidence suggests that the initial event in infections is the adherence of microorganisms to epithelial cells of mucosal surfaces (Beachy, 1981). Organisms that are unable to adhere to mucosal surfaces fail to colonize because they are removed by the secretions that bathe the mucosal surfaces (Beachy, 1981). The adherence process is dependent upon the specific recognition between bacteria and epithelial cells, mediated through adhesin molecules present on the bacterial cell surface and receptors present on target cells.

Molecules which have been identified as adhesions in *P. aeruginosa* include alginate and pilus proteins. *P. aeruginosa* utilizes both pili and alginate (the principle component of the *P. aeruginosa* capsule) as adhesins to mediate attachment to human respiratory epithelial cells (Doig, et al., 1990). Pili have been identified as an important adhesive factor for buccal cells (Woods, et al., 1980), damaged tracheal epithelium (Ramphal, et al., 1984), and mucous proteins (Ramphal, et al., 1987). In particular, a specific peptide domain of the pilus protein has been recognized as a determinant of the adhesive properties of these *P. aeruginosa*.

Gangliosides, and in particular, gangliotriosylceramide (GgO$_3$; GalNacβ1-4Galβ1-4Glcβ1-1Cer), gangliotetraosylceramide (GgO$_4$; Galβ1-3GalNAcβ1-4Galβ1-4Glcβ1-1Cer), and lactosylceramide (LacCer; Galβ1-4Glcβ1-1Cer) have been identified as possible receptors for *P. aeruginosa* (Baker, 1989; Krivan, et al., 1988a), but the adhesin or adhesins responsible for this specificity have not been identified. *P. aeruginosa* can utilize both pili and alginate (the principle component of the *P. aeruginosa* capsule) as adhesins to mediate attachment to human respiratory epithelial cells (Doig, et al., 1990). However, strains exist which lack both pili, and ability to synthesize alginate and which still retain the capacity to attach to epithelial cells, thereby suggesting the existence of additional adhesin molecules.

Earlier filed co-pending and co-owned U.S. patent applications (Ser. Nos. 07/638,492 and 07/727,797, which is a continuation of Ser. No. 07/344,565, now abandoned) disclose *P. aeruginosa* peptides derived from the C-terminal region of the *P. aeruginosa* pilin protein, and specifically, the C-terminal region which includes two Cys residues and the intervening amino acid residues. The derived region of representative peptides vary in length between 14 and 19 amino acid residues, including the two Cys residues, and are prepared in both oxidized (disulfide-linked) and reduced (non-cyclized) form. The peptides (in both reduced and oxidized form) were shown to have the following properties: (a) the ability to bind to human tracheal epithelial cells (TECs) and human buccal epithelial cells (BECs); (b) the ability to inhibit binding of Pseudomonas pilin peptide to tracheal epithelial cells (TECs) and buccal epithelial (BECs); (c) the ability to elicit serum antibodies which are immunoreactive with Pseudomonas pilin peptide; and (d) the ability to elicit serum antibodies which block binding to Pseudomonas pilin peptide to BECs; and (e) ability to inhibit binding of unrelated bacterial and fungal organisms to human BECs and/or tracheal epithelial cells (TECs).

It was further shown, in studies conducted in support of these applications, that monoclonal antibodies prepared against the Pseudomonas-derived peptide were effective in blocking fungal cell adherence to BECs.

It has now been discovered that exoenzyme S (Exo S), a bacterial toxin having ADP ribosyl transferase activity which is present on the surface of *P. aeruginosa* cells, also binds to BECs with a specificity which is similar to that exhibited by bacterial cells. Antibodies which are directed against the pilus peptide domain earlier recognized as a determinant of bacterial binding cross-react with purified Exo C. The binding region includes a segment of the amino acid sequence of Exo S having about 60–70% sequence homology with the above-pilus peptide domain found to be a determinant of bacterial binding to target cells.

These combined findings show that Exo S-derived peptide, and antibodies produced in response to the peptides, are capable of inhibiting infections in which the infecting microorganisms have surface proteins which are immunologically cross-reactive with antibodies produced against the peptide region of Exo S protein.

SUMMARY OF THE INVENTION

The invention includes, in one aspect, a method of preventing infection by *Pseudomonas aeruginosa* and immunologically related organisms in a subject. One method described by the invention is a passive immunization method effective against Pseudomonas which includes administering to a subject an antibody characterized by specific immunoreactivity with an Exo S peptide epitope formed by the sequence SEQ ID NO: 2. In another embodiment, the antibody is further characterized by its ability to inhibit binding of Pseudomonas to human epithelial cells. In another embodiment, the passive immunization method of the invention includes administering to the subject an antibody which is reactive with a peptide epitope which includes the sequence SEQ ID NO: 2. In yet another embodiment, the passive immunization method includes administration of a monoclonal antibody produced by a hybridoma selected from the group consisting of Exo S-28, Exo S-40, Exo S-50 and Exo S-141.

In a related aspect, the invention includes a method of producing immunity against infection by *Pseudomonas aeruginosa* and immunologically related microorganisms. In this method, a peptide containing an epitope formed by the sequence SEQ ID NO: 2 is administered to a patient in a pharmaceutically expedient excipient. The peptide used in the vaccine is further characterized by (a) immunospecific binding to monoclonal antibody PK99H or MCA1; (b) a peptide length less than 20 amino acid residues; and c) ability to block binding of *Pseudomonas aeruginosa* to buccal epithelial cells.

In a preferred embodiment, peptide used in this method of the invention has an immunogenic epitope contained in the sequence SEQ ID NO: 2, where the two cysteine residues (C) are linked covalently. In yet another embodiment, the peptide may be further recognized by monoclonal antibody MCA.

In still a further embodiment of the invention, the peptide used in the method of the invention includes the sequence SEQ ID NO: 2, where the two cysteine residues (C) are linked covalently.

Alternatively, the method of the invention may employ a peptide having an epitope which includes the sequence C A T T A T G P N G S C.

The invention includes, in still another aspect, a peptide containing an epitope formed by the sequence SEQ ID. NO: 2.

The peptide of the invention is further characterized by (a) immunospecific binding to monoclonal antibody PK99H or MCA1; (b) a peptide length less than 20 amino acid residues; and (c) ability to block binding of *Pseudomonas aeruginosa* to buccal epithelial cells.

In another aspect, the peptide of the invention includes the sequence SEQ ID NO: 2.

These and other objects and features of the present invention will become more fully apparent when the following detailed description of the invention is read in conjunction with the accompanying drawings.

BRIEF DESCRIPTION OF THE DRAWINGS

FIG. 1A shows the amino acid sequence of residues 131–143 (SEQ ID NO: 3) of the pilin protein from *P. aeruginosa* strain PAK in three-letter amino acid code, where —S—S— designates the presence of a disulfide linkage, and where in parentheses is shown in single letter amino acid code substitutions to this sequence which are a composite of internally consistent amino acid variations of the homologous regions of the pilin proteins derived from five strains of *P. aeruginosa* (PAK, PAO, CD4, K122, and KB7):

FIG. 1B shows the Exo S-derived peptide of the invention (SEQ ID NO: 2) in three letter amino acid code, where —S—S— designates the presence of a disulfide linkage, and for purposes of comparison, the amino acid substitutions (shown in one letter code) of the analogous region of the pilin peptides described in FIG. 1A;

FIGS. 2A and 2B show immunoelectron microscopy of *P. aeruginosa* cells exposed to monoclonal antibody raised against purified Exo S (2A) or phosphate buffered saline (2B) followed by protein A-colloidal gold;

FIG. 8 shows 1 letter code amino acid sequences of Pseudomonas pilin peptides derived from strains PAK (SEQ ID NO: 5), PAO (SEQ ID NO: 6), P1 (SEQ ID NO: 7), KB7 (SEQ ID NO: 8), K122-4 (SEQ ID NO: 9), CD4 (SEQ ID NO: 10), GA (SEQ ID NO: 11) and 492c (SEQ ID NO: 12).

DETAILED DESCRIPTION OF THE INVENTION

1. Definitions

Figure 3:
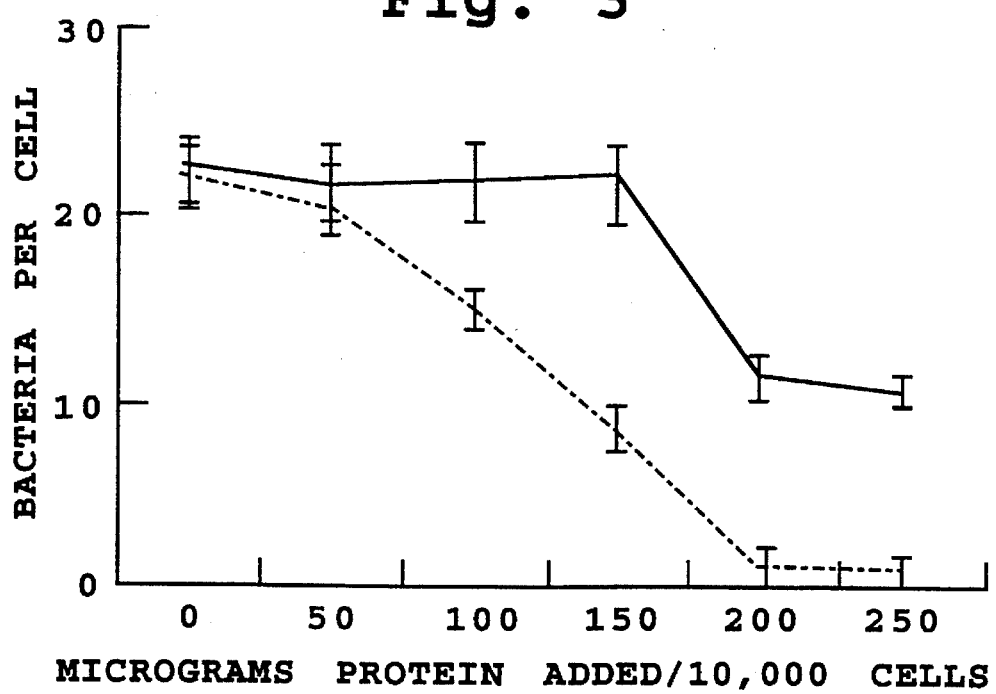
FIG. 3 is a plot showing the effect of purified Exo S (dotted line) or purified pili (solid line) to block adherence of intact *P. aeruginosa* strain DG1 to buccal epithelial cells.

The terms "epitope" and "epitopic" as used herein, designate the structural component of a molecule that is responsible for specific interaction with corresponding antibody (immunoglobulin) molecules elicited by the same or related antigen. More generally, the term "epitope", as used herein, refers to a peptide having the same or similar immunoreactive properties, such as specific antibody binding affinity, as the antigenic protein or peptide used to generate the antibody. Therefore, an epitope which is formed by a specific peptide sequence generally refers to any peptide which is reactive with antibodies directed against the specific sequence, which antibodies are reactive with the specific sequence.

The term "antigen" as used herein, means a molecule which is used to induce production of antibodies. The term is alternatively used to denote a molecule which is reactive with a specific antibody.

The term "immunogen" as used herein, describes an entity that induces antibody production in the host animal. In some instances the antigen and the immunogen are the same entity, while in other instances the two entities are different.

The term "immunologically mimics" is used herein to mean that an immunogenic polypeptide of this invention is not a natural protein or a cleaved fragment of a natural protein, but a manufactured polypeptide, as by solid phase synthesis or genetic engineering techniques, which polypeptide induces production of antibodies that bind to the inducing polypeptide and also to a corresponding pilin or pilin polypeptide portion.

All amino acid residues identified herein are in the natural or L-configuration unless otherwise specified. In keeping with standard peptide nomenclature, abbreviations for amino acid residues are standard 3-letter and/or 1 letter codes commonly used in the art.

The terms "glycosphinogolipids", "GSL" and "gangliosides" are used interchangeably to describe a sphingolipid consisting of a ceramide having an attached oligosaccharide chain containing at least one acidic sugar. A common acidic sugar is N-acetylneuraminate, which is also known as "sialic acid". Asialo GM1 refers to the ganglioside GM1 from which the sialic acid has been removed, which is also technically termed "cerebroside". Abbreviations used to describe the sugar substitutions found in gangliosides and in polysaccharides include Gal, galactose; Glc, glucose; GalNac, N-acetylgalactosamine; and NAN, N-acetylneuraminate.

2. Exo S

Exo S is a polypeptide toxin which has been shown to be present in the outer surface of *P. aeruginosa* cells. The enzyme has catalytic (ADP ribosylation) as well as cytotoxic properties which are separable, as described in section 4 below. Purification and cloning of this enzyme toxin have been achieved (Woods, et al., 1987, 1990), and the partial DNA sequence of the HinSai fragment of the cloned gene has been used to identify a region having relative sequence homology to known adhesion domains residing in the pilin proteins of *P. aeruginosa*. The DNA and predicted amino acid sequence of the homologous segment of the ExoS are presented as SEQ ID NO:1 and SEQ ID NO:2, respectively.

The amino acids represented in boldface and underlined are amino acids that are homologous to those found in pilin (KB7). The significance of this homology is that the amino acid sequence in pili bounded by the cysteine residues has been shown to be the epithelial binding domain of pili. As will be shown below, Exo S is also an adhesin which binds to the same receptors as do pilin proteins and peptide fragments.

Purified ExoS was additionally utilized in experiments comparing its ability with that of purified pili to compete with intact Pseudomonas cells for adherence to buccal epithelial cells (BECs). Experimental protocols for these experiments are described in Example 5. FIG. 3 shows the results of experiments in which Exo S and purified PAK pili were compared for ability to compete for binding of intact *P. aeruginosa* strain DG1 to BECs. Incubation of buccal cells with purified Exo S inhibited the binding of bacteria to the cells in a concentration-dependent manner (FIG. 3, dashed line). When present at a concentration of 200 µg of protein/10,000 cells Exo S inhibited virtually all binding of bacterial cells to BECs, whereas the same concentration of purified pili reduced adherence only by approximately 50% (see FIG. 3, solid line).

3. *P. aeruginosa* Pilin and Exo S Peptides

FIG. 1A shows the amino acid sequence of residues 131–143 of the pilin protein from *P. aeruginosa* strain PAK in three-letter amino acid code. Shown in parentheses in one-letter amino acid code are substitutions to this sequence which are a composite of internally consistent amino acid variations of the homologous regions of the pilin proteins derived from five strains of *P. aeruginosa* (PAK, PAO, CD4, K122, and KB7). These sequences and the composite peptide were reported in co-pending U.S. patent application Ser. No. 08/638,492, filed Jan. 4, 1991, which is incorporated herein by reference. In that application, it was noted that the internal-variation substitutions are those substitutions found in nature, and are therefore apparently compatible with requisite antigenic properties of the peptide. Thus, for example, in the composite pilin peptide of FIG. 1A, the residue immediately C-terminal to the N-terminal Cys could alternatively be Threonine, Lysine or Alanine.

The sequences shown in FIG. 1A form a portion of peptide comprising residues 131–143 of the pilin protein. Peptides having sequences characterized by the composite peptide of the invention, comprising residues 128–144 of the pilin protein were shown to be useful in inhibiting adhesion of *P. aeruginosa* and related organisms to epithelial cell targets, and in producing vaccines suitable for protecting an organism from infections caused by such organisms.

Partial sequencing of a DNA clone of purified Exo S, described in Examples 1 and 2, has revealed a sequence, shown in FIG. 1B in three-letter amino acid code, which is partially homologous to the pilin peptide region 131–143, described above. This peptide, and more particularly, the epitope formed by the sequence of this peptide, is referred to herein as Exo S peptide. Also shown in FIG. 1B, for purposes of comparison, are the amino acid substitutions (shown in one letter code) of the analogous region of the pilin peptide described above. From these sequence comparisons, and the cross-reactivity studied described herein, it is appreciated that certain amino acid substitutions can be made in the Exo S peptide sequence as shown without disrupting the epitopic nature of the peptide. That is, as defined herein, an Exo S peptide epitope refers to a peptide which exhibits substantially the same or higher binding affinity to an antibody directed against the primary sequence (SEQ ID NO: 2). According to an important feature of the present invention such epitopic peptides are generally as useful in the production of vaccines or antibodies for passive immunization as is the primary sequence peptide. Thus, for example, with reference to FIG. 1B, it is appreciated that a threonine (T) or lysine (K) residue might be substituted for the alanine at position 2 in the Exo S peptide; alternatively, or in addition, a serine (S) might be substitued for the threonine at position 3.

As is described further below, it has now been discovered that Exo S displays cross immunoreactivity with antibodies which are directed to the Pseudomonas-derived pilin peptides described above. Such antibodies, and in particular, one known as monoclonal antibody PK99H (Mab PK99H), which was described in the co-pending U.S. patent application Ser. No. 07/638,492 described above, have the ability to block binding *P. aeruginosa* and its pili to target epithelial cells. Furthermore, certain antibodies directed against Exo S or Exo S peptide are cross-reactive with *P. aeruginosa* pili and can inhibit binding of *P. aeruginosa* to epithelial cells.

According to one aspect of the invention, Exo S peptide shares with pilin peptides the ability to (a) react with monoclonal antibody PK99H and (b) block binding of *P. aeruginosa* and microorganisms sharing reactivity with Mab PK99H to epithelial cells. In addition, the Exo S peptide of the invention can be bound by a monoclonal antibody identified as Mab MCA1, with consequent inhibition of the binding to epithelial cells.

The PK99H Mab was prepared against PAK pili. This Mab was demonstrated in co-pending, co-owned U.S. patent application U.S. Ser. No. 07/638,492 to bind a specific C-terminal region of PAK pilin protein comprising SEQ ID NO: 4, described herein. This particular peptide is included in *Pseudomonas aeruginosa*(PAK) pilin protein residues 128–144. PK99H was also been shown in the aforementioned co-pending patent application to be cross-reactive with various other *P. aeruginosa* strain pili. The requirement that the peptide of the invention exhibit cross-reactivity with this antibody ensures that the peptide has requisite epitopic similarity to the pilin peptides shown to block adhesion of *P. aeruginosa* to epithelial cells.

As will be described below, the epitopic region of the Exo S peptide has the ability to bind to a receptor site on human buccal epithelial cells (BECs), and this binding is effective to inhibit *P. aeruginosa* binding to these epithelial cells. The requirement for peptide epitope binding to these cells ensures that the peptide has the requisite receptor binding activity.

Peptides of the invention are conveniently synthesized by conventional solid phase synthetic methods, as described in Example 3. Alternatively, peptides of the invention may be produced by recombinant means, using the cloning vectors and sequences described in Example 2. The peptides of the invention may contain additional N-terminal or C-terminal residues, consistent with the above constraints.

4. Anti-Exo S Antibodies

This section summarizes methods of production, and antibody binding characteristics of polyclonal and monoclonal antibodies which are immunoreactive with the peptides of the invention. The antibodies are useful in producing passive immunity in an organism to pathogens which have adhesin molecules characterized by epitopes formed by Exo S peptide.

A. Polyclonal Antibodies

Polyclonal antibodies specific against reduced and oxidized forms of PAK peptide were prepared as described in the earlier-filed co-pending application, and as published (Lee, et al., 1989). Briefly, PAK peptides were conjugated to keyhole limpet hemocyanin (KLH), and the conjugate was used to immunize female Flemish rabbits. The peptides include the PAK peptide in reduced ($PAK_{red}$) and oxidized form ($PAK_{ox}$) form. Rabbits were given an initial immunization, two weeks later given a booster immunization, and then bled two weeks later. An immunoglobulin fraction was purified by Protein A affinity chromatography. Antibody binding to native PAK pilin protein, PAK peptide, and PAO peptide, was examined by standard ELISA procedures (Worobec, et al., 1985). Antibody specifications were as follows: (a) the antisera produced by both $PAK_{ox}$ and $PAK_{red}$ was able to bind native PAK pili, and the titers raised against both peptides were similar; (b) the antisera raised against the $PAK_{ox}$ peptide was strongly cross-reactive with native PAO pili; and (c) the antisera raised against the $PAK_{ox}$ peptide was only weakly cross-reactive with native PAO pili.

The results show that, although both oxidized and reduced forms of the peptide are effective to induce antibodies which are reactive with same-species pilin protein, the oxidized (disulfide-linked) form of the peptide is important for stimulating production of antibodies which are cross-reactive with pilin proteins from other *P. aeruginosa* strains.

Polyclonal antibodies to purified Exo S (polyclonal anti-Exo S) were prepared and published by Woods, et al. (1987), using New Zealand rabbits. In some cases, antisera were adsorbed with *P. aeruginosa* strain DG-ExS5, deficient in production of Exo S (Woods, et al., 1985), prior to use.

Figures 2A, 2B:
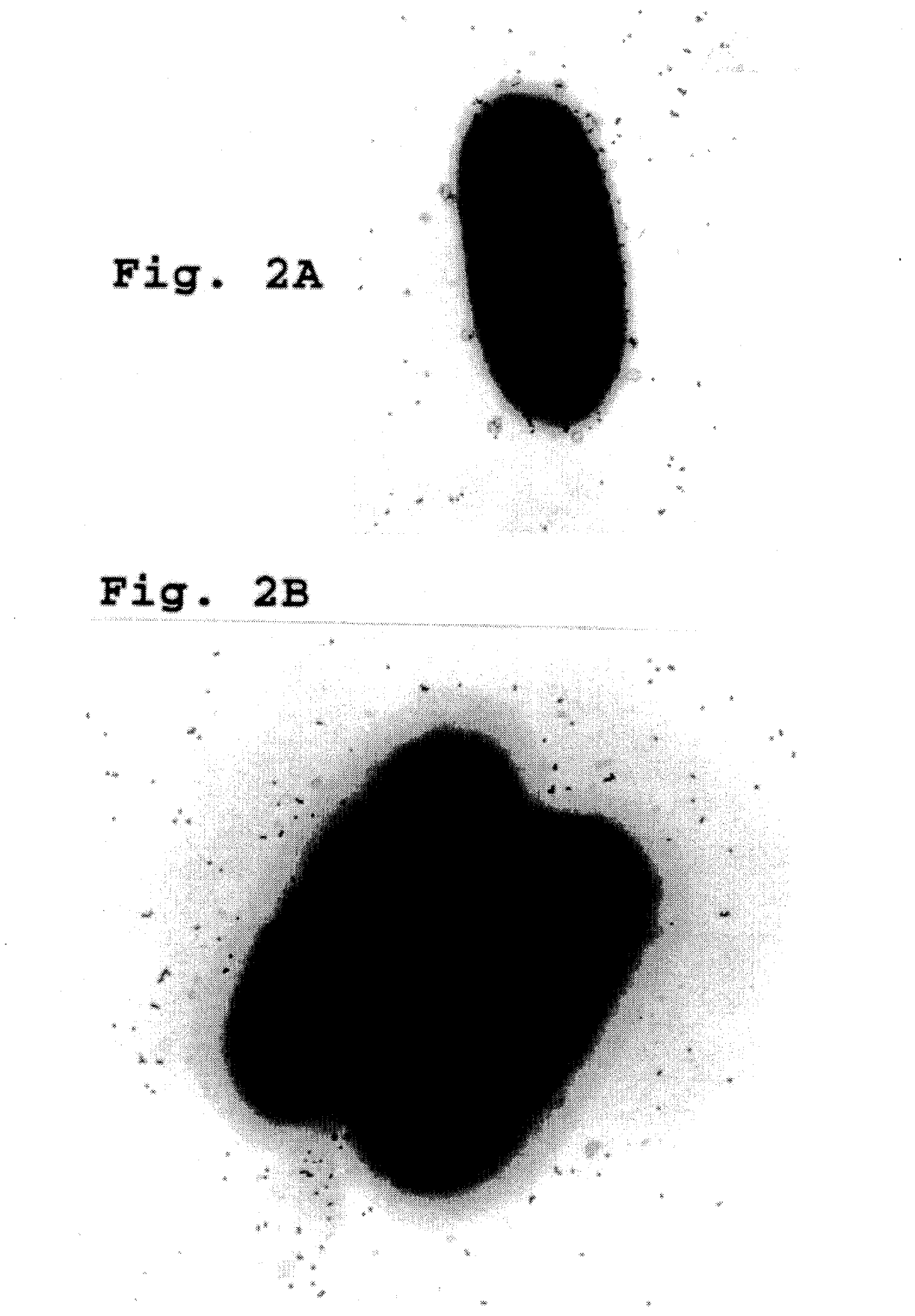

The presence of Exo S on the surface of *P. aeruginosa* was confirmed by the immunolabeling experiments illustrated in FIGS. 2A and 2B. In this experiments, bacterial cells were exposed to polyclonal anti-Exo S (2A) or saline carrier, prior to colloidal gold conjugated to protein A or anti-rabbit IgG. Gold beads were observed as a uniform coating on the cell surfaces of those cell preparations exposed to anti-Exo S (FIG. 2A). In contrast, control cells incubated in the absence of antibody to Exo S did not reveal any beads on the cell surfaces (FIG. 2B).

Polyclonal antibodies to Exo S were additionally utilized in experiments examining their cross-reactivity with pili derived from *Pseudomonas aeruginosa* strains PAK, PAO, and P1 and with pilin peptide PAK(128–144)$_{ox}$ described in detail below (Table 2) and in Example 6. Polyclonal antibodies to PAK, and to PAK pilin peptide PAK(128–144)$_{ox}$ were also tested for cross-reactivity with various pili, and with Exo S.

B. Monoclonal Antibodies

1. Anti-pilin antibodies

Monoclonal antibodies against native PAK pili protein were prepared according standard methods (Doig, et al., 1989) and detailed in Example 4 (part B.2). Briefly, BALB/c mice were immunized with weekly injections of PAK pili. Spleen cells from the animals were fused with mouse myeloma cell line NS1 (Irvin, et al., 1985), and successful fusions were screened by an ELISA method for ability to secrete anti-pilin antibody. A library of 262 hybridoma clones that secreted antibodies immunoreactive with PAK pili were obtained. Protein A purified monoclonal antibodies were then screened against pilin peptide fragments (Doig, et al., 1989), to determine specificities of these antibodies. Four hybridoma cell lines were selected for further specificity studies, cell lines PK99H, PH34C, PK3B, and PK41C.

Immunoblots of purified PAK and PAO pili revealed that PK99H and PK3B Mabs were specific for PAK pilin protein, while PK34C and PK41C Mabs were immunoreactive with both PAK and PAO pilin peptide. PK99H and PK34C Mabs were both immunoreactive with C-terminal fragment of PAK pilin.

In co-pending U.S. patent application Ser. No. 07/638, 492, Fab fragments prepared from PK99H and PK34C were shown to inhibit Pseudomonas pili binding to BECs, indicating their specificities for the adhesin domain of the pilin protein.

2. Anti-Exo S antibodies

Monoclonal antibodies to purified Exo S were prepared as published elsewhere by the inventors (Woods, et al., 1987) and detailed in Example 4B. Briefly, antigen for injection was prepared from a purified preparation of Exo S which was subjected to dialysis against 1% formalin in 0.1M Tris buffer (Ph 8.0) and 0.2M L-lysine, followed by dialysis against 0.2M L-lysine in 0.85% NaCl, Ph 6.3 prior to injection into BALB/c mice. Dispersed spleen cells from the mice were fused with NS-1 cells using 50% (wt/wt) polyethylene glycol (WM 1500). Supernatants of fused cells in culture were tested for production of antibody to Exo S, using an ELISA procedure. Positive cell lines were subcloned extensively and were injected into pristane primed mice for ascitic tumor production. Antibodies present in ascitic fluid were purified and immunoreactivity was verified using purified Exo S in Western blots.

Monoclonal antibodies to Exo S were additionally tested for ability to (a) inhibit enzyme (ADP ribosylation) activity, and (b) neutralize cytotoxic effects of Exo S, as described by Woods, et al. (1987) and detailed in Example 9. Monoclonal antibody MCA1 was able to neutralize cytotoxic activity, but has relatively low potency in inhibition enzyme activity. Monoclonal antibody MCA2 was found to have much greater potency in inhibition of enzyme activity, but relatively low potency in neutralizing the cytotoxic effects of Exo S. MCA2 was subsequently used in purification of the protein (Woods, et al., 1987). Monoclonal antibody MCA3 was shown to inhibit enzyme activity, but not neutralize cytotoxicity.

In experiments testing the ability of anti-Exo S monoclonal antibodies to interfere with binding of *P. aeruginosa* to BECs, it was found monoclonal antibody MCA1, which neutralizes the cytotoxicity of Exo S, but has no affect on enzymatic activity, reduced adherence of bacteria to background levels (Table 1). Monoclonal antibody MCA3, which neutralizes enzymatic activity but not cytotoxicity, did not inhibit the adherence of Exo S to buccal cells.

TABLE 1

Effect of Monoclonal Antibodies to Purified Exo S on *Pseudomonas aeruginosa* Adherence to Buccal Epithelial Cells

| Monoclonal Antibody[1] | Strain | Adherence[2] |
| --- | --- | --- |
| None-control | PAO | 22.1 ± 2.5 |
| None-control | DG1 | 26.7 ± 3.4 |
| MCA1[3] | PAO | 1.7 ± 0.3[4] |
| MAC1 | DG1 | 0.8 ± 0.1[4] |
| MCA3[5] | PAO | 21.9 ± 3.6 |
| MCA3 | DG1 | 25.8 ± 4.2 |

[1]Monoclonal antibodies prepared as previously described.
[2]Adherence assay performed as described. Values represent mean ± S.D.
[3]Neutralizes cytotoxicity but not enzymatic activity.
[4]Significantly different from control (p > 0.01).
[5]Neutralizes enzymatic activity but not cytotoxicity.

3. Anti-Exo S peptide antibodies

Anti-Exo S peptide monoclonal antibodies were prepared as described in Example 4B.3, using as antigen a conjugate of Exo S peptide having the sequence SEQ ID NO: 1 and tetanus toxin (TT). Hybridoma supernatants were tested for presence of antibodies immunoreactive by ELISA test with the antigen. At least 141 positive clones were detected in the fusion of three spleens. Four clones of interest were further subcloned and deposited in the cell depository of the Department of Medical Microbiology and Infectious Diseases of the University of Alberta, Alberta, Canada. These clones are identified by cell lines Nos. Exo S-28, Exo S-40, Exo S-50, and Exo S-141. Supernatants from the clones were tested for cross-immunoreactivity with Pseudomonas derived antigens, as described in the following sections.

5. Immunocross-reactivity of Antibodies to Exo S and Pilin Proteins a. Anti-pilin antibody reactivity with Exo S Direct ELISA experiments were performed to examine immunocross-reactivity between antibodies to pilin proteins and to Exo S and their respective antigens. Table 2 shows the results of experiments in which the antigens listed in column 2 of the table were coated on microtiter plates. After appropriate blocking and washing of the plates, as described in Example 6A, serial dilutions of the antibodies listed in column 1 of the table were added to and incubated in the coated wells. The presence of bound antibody was detected by addition of an appropriate enzyme-conjugated species-appropriate second antibody and enzyme substrate capable of producing a color reaction. Titers with respect to the antigen tested were determined by noting the highest serial dilution of antibody at which a significant color reaction was detected. Thus, in the case of PAK pili antigen, a reaction was detected with Mab PK99H at greater than $10^6$ fold dilution of the stock antibody solution. In contrast, using PAK pili as antigen, polyclonal antiserum to Exo S (anti-Exo S) yielded a detectable signal at $4 \times 10^4$ fold dilution of serum. This titer may be referenced to the titer of anti-Exo S determined ($3.2 \times 10^6$) when Exo S itself was used as an antigen. From Table 2 the following interactions are apparent: (a) Mab PK99H recognizes PAK pili>Exo S>P1 pili, and does not recognize PAO pili; (b) polyclonal antibody to PAK pili recognizes PAK pili=Exo S and does not appreciably recognize PAO pili or P1 pili; (c) polyclonal antibody to pilin peptide (128–144)ox derived from PAK pili recognizes PAK peptide (128–144)ox>PAK pili>Exo S>P1 pili; and (d) polyclonal antibody to Exo S recognizes Exo S>PAK (128–144)ox=PAK pili=PAO pili>P1 pili. It is apparent from this analysis that the Exo S antibody is generally reactive with pilin-associated adhesin components of Pseudomonas.

is immunoreactive with a number of Pseudomonas pilin peptides, including PAK (*P. aeruginosa* strain K) pilin peptide having the sequence illustrated in FIG. 8 as SEQ ID NO: 5. The antibody was purified from mouse ascites fluid by Protein G affinity high performance liquid chromatography.

The PK99H antibody was coated onto the wells of microtiter plates, according to methods detailed in Example 6.3. The biotin-Exo S peptide was serially diluted and added to the wells. The amount of biotin-ExoS peptide bound to the immobilized PK99H monoclonal antibody was then determined. An end-point titer of the solution of about 10-4 was measured in this manner, indicating reactivity between the Exo S peptide and monoclonal antibody PK99H.

c. Anti-Exo S antibody reactivity with Pseudomonas pili

Competitive ELISA assays were carried out to further examine the ability of anti-Exo S antibodies to distinguish between heterologous binding sites. Methods used in this analysis are described in Example 6B. Briefly, microtiter plate wells were coated with purified PAK or PAO pili, blocked, and washed to remove unbound materials. Test competitor was then mixed and pre-incubated with a concentration of anti-Exo S polyclonal antibody sufficient to produce less than or equal to 50% of maximal binding signal, when anti-Exo S antibody was added in the absence

TABLE 2

Cross-Reactivity of anti-pilus and anti-Exo S antibodies with *Pseudomonas aeruginosa* Pili and Exo S Direct ELISA Data

| Antibody | Antigen: PAK pili Titre |
| --- | --- |
| PK99H | $>>10^6$ |
| Polyclonal anti-PAK | $>>10^6$ |
| Polyclonal anti-Exo S | $4 \times 10S4$ |
| Polyclonal anti-PAK(128–144)$_{ox}$ | $>>10^6$ |
| Antibody | Antigen: PAO pili Titre |
| PK99H | NE |
| Polyclonal anti-PAK | NE |
| Polyclonal anti-Exo S | $4 \times 10^4$ |
| Polyclonal anti-PAK(128–144)$_{ox}$ | × |
| Antibody | Antigen: P1 pili Titre |
| PK99H | $1.1 \times 10^4$ |
| Polyclonal anti-PAK | NE |
| Polyclonal anti-Exo S | $1.1 \times 10^4$ |
| Polyclonal anti-PAK(128–144)$_{ox}$ | $1.1 \times 10^4$ |
| Antibody | Antigen: Exo S Titre |
| PK99H | $1.6 \times 10^5$ |
| Polyclonal anti-PAK | $>>10^6$ |
| Polyclonal anti-Exo S | $3.2 \times 10^6$ |
| Polyclonal anti-PAK(128–144)$_{ox}$ | $3.2 \times 10^6$ |
| Antibody | Antigen: Bsa-PAK(128–144)$_{ox}$ Titre |
| PK99H | ND |
| Polyclonal anti-PAK | ND |
| Polyclonal anti-Exo S | $4 \times 10^4$ |
| Polyclonal anti-PAK(128–144)$_{ox}$ | $6.4 \times 10^7$ | b. Anti-pilin antibody reactivity with Exo S peptide

Reactivity of Exo S peptide with anti-pilin antibodies was also demonstrated in experiments carried out in support of the present invention. Briefly, biotinylated ExoS peptide was prepared as detailed in Example 6.3. Monoclonal antibody PK99H, previously described in co-owned U.S. patent application for "Pseudomonas Peptide Composition and Method", Ser. No. 07/638,492, filed Jan. 4, 1991, was tested for reactivity with the Exo S peptide. The PK99H antibody of competitor. The test mixture was then added to wells of the microtiter plate.

Figure 4A:
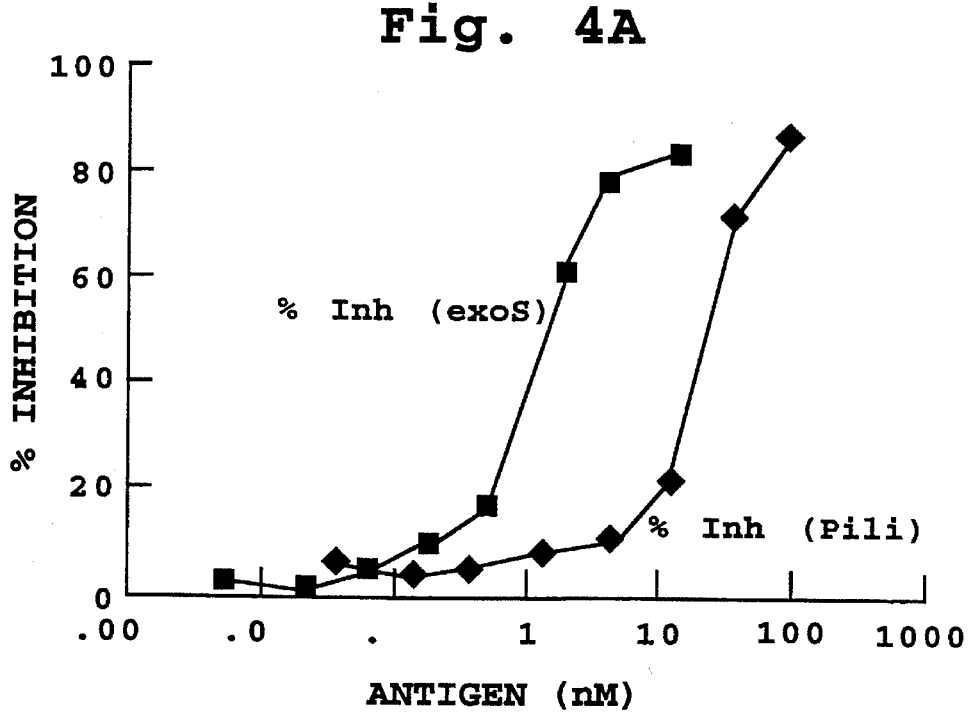
FIGS. 4A and 4B show the results of competitive ELISA experiments comparing abilities of PAK pili (4A) or PAO pili (4B) to Exo S to compete for binding of polyclonal anti-Exo S to PAK pili.

FIG. 4A shows the results of experiments in which PAK pili were used as plate coating and test competitor. As seen, Exo S was more potent than were PAK pili in interfering with binding between anti-Exo S antibody and PAK pili. In contrast, it can be seen in FIG. 4B that Exo S and PAO pili were essentially equipotent in interfering with binding of anti-Exo S antibody to PAO pili coated in the wells.

Anti-Exo S peptide antibodies were also tested for cross-immunoreactivity with various Pseudomonas antibodies. Table 3 shows absorbance readings in an ELISA in which monoclonal antibodies produced by hybridoma cell lines Exo S-28, Exo S-40, Exo S-50, and Exo S-141 were tested for reactivity with the antigens listed (reading across the top of the table). Antigens tested included purified pili from *Pseudomonas aeruginosa* strains PAK, PAO, P1, KB7, and K122-4 (designated "strain-pili"), conjugates of peptides derived from strains PAK, PAO, P1, KB7, K122-4, and CD4 (shown in FIG. 8 as SEQ ID Nos 5-10) and from Exo S peptide conjugated to bovine serum albumin (BSA) (designated "peptide-BSA"), native exo S protein ("Exo S"), and a conjugate of BSA and a PAK pilin peptide having the sequence presented as SEQ ID NO: 4, designated "1K043" in the table. This latter peptide was shown to comprise a core epitope of the PAK pilin sequence recognized by monoclonal antibody PK99H in co-pending, co-owned U.S. patent application U.S. Ser. No. 07/638,498, which is incorporated herein by reference.

As demonstrated by the experiments shown here, significant reactivity was observed between antibodies prepared against ExoS peptide and pilin-derived peptides from a number of Pseudomonas strains, evidenced by absorbances greater than about 0.200 absorbance units. These experiments demonstrate the usefulness of antibodies produced against Exo S peptide in binding to bacterial cells. More particularly, since, as described in the aforementioned co-pending, co-owned patent application U.S. Ser. No. 07/638,498, the particular pilin peptide regions have been shown to be important in adhesion between the bacteria and their epithelial cell binding sites, it is noted that anti-Exo S peptide antibodies react with and therefore interfere with binding mediated through this region of the bacterial cell. Moreover, monoclonal anti-pilus antibody PK99H, described herein and in co-pending, co-owned U.S. patent application U.S. Ser. No. 07/638,498, is effective in vitro to inhibit Pseudomonas binding to BECs and is also effective in vivo to protect against infection by Pseudomonas (c.f., Example 8 and Part 7, herein). It is a discovery of the present invention that anti-Exo S protein and anti-Exo S peptide antibodies having similar peptide immunoreactivity to the reactivity exhibited by PK99H have similar in vitro and in vivo properties to that antibody.

binding to antigen. Binding of both the intact bacterial cells and the isolated enzyme to $GgO_4$ (gangliotetraosylceramide; Gal$\beta$1-3GalNAc$\beta$1-4Gal$\beta$1-4Glc$\beta$1-1Cer) (asialoGM1) and LacCer (lactosylceramide; Gal$\beta$1-4Glc$\beta$1-1Cer) was clearly evident from the studies, as was binding to the trihexosylceramide region of the dog mucosa sample. Binding to $GgO_3$ (gangliotrisylceramide; GalNac$\beta$1-4Gal$\beta$1-4Glc$\beta$1-1Cer; asialo-GM1) was also detected (not shown). No bands were detected if the overlay with Exo S was omitted from the assay. This binding specificity is in agreement with previously published reports for many strains of *P. aeruginosa* (Baker, et al., 1990; Krivan, et al., 1988b). Neither Exo S nor strain DG1 bound to the sialylated GSLs, $GM_1$, or $GM_2$.

Binding of Exo S to GSLs is described in Example 7B (1). Binding curves of Exo S to dilutions of GLSs immobilized on plastic plates shown in FIG. 5 revealed optimum binding at approximately 1 μg of $GgO_4$ (ASGM-1, asialoGM1). The reduced binding at 10 μg $GgO_4$ is most likely an artifact of the assay related to the coating of the plate at high concentrations of GSL, since this phenomenon is also observed with whole bacteria (not shown).

B. Binding of Pili to GSLs

Figure 6A:
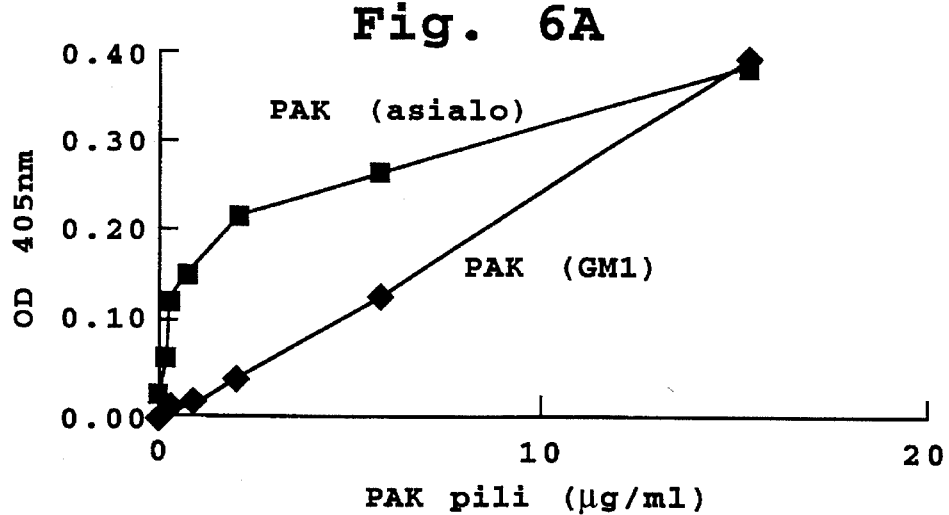
FIGS. 6A, 6B, and 6C show a plot of binding of PAK pili (6A), PAO pili (6B), and purified Exo S (6C) to glycosphingolipids mono- and asialo-GM1.
Figure 6B:
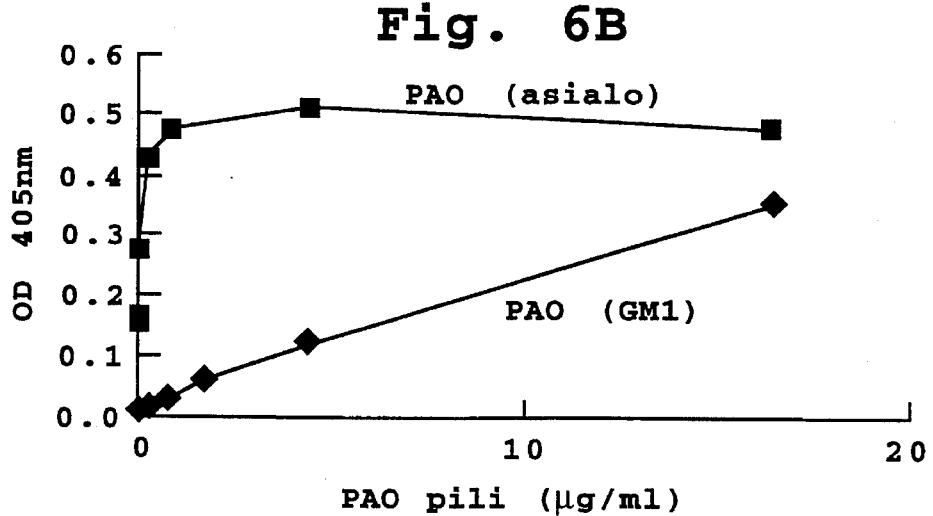
Figure 6C:
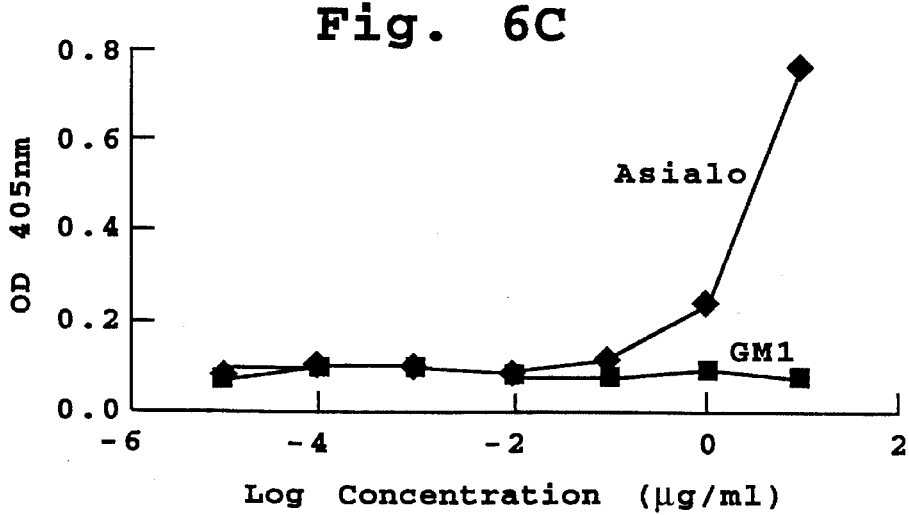

A solid phase GSL binding assay described in Example 7B was used to assess binding of purified pili to mono- and asialo-GM1. In this assay, GSLs were adsorbed to the wells of 96-well microtiter plates, washed and exposed to test agent. Presence of bound agent was detected by subsequent addition of an appropriate agent-specific antibody, followed by enzyme conjugated second antibody. Binding of PAK pili, PAO pili, and for comparison, Exo S to asialo GM1 and monosialo GM1 is shown in the binding curves represented in FIGS. 6A, 6B, and 6C, respectively. In the plots shown in FIGS. 6A and 6B, binding to monosialo GM1 is represented by solid diamonds, and binding to asialo-BM1 is presented by open squares. In the plots shown in FIG. 6C, binding to monosialo GM1 is represented by open squares, and binding to asialo-GM1 is represented by closed triangles. Apparent $K_m$'s os binding to each of these species were calculated from reciprocal plots of the binding data. A summary of the $K_m$ values (which represent the approximate concentration of ligand required to saturate 50% of the receptor sites under the experimental conditions) is given in Table 4.

TABLE 3

| | Immunoreactivity of Monoclonal Antibodies[1] | | | | | | | | | | | | | |
|---|---|---|---|---|---|---|---|---|---|---|---|---|---|---|
| Hybridoma Cell Line | PAK-pili | PAK-BSA | PAO pili | PAO-BSA | PI pili | PI-BSA | KB7 pili | KB7-BSA | K122-pili | K122-BSA | Exo S | Exo S BSA | 1K043 | CD4-BSA |
| Exo S-28 | 0.369 | 0.317 | 0.860 | 0.207 | 0.784 | 0.280 | 0.434 | 0.451 | 0.287 | 0.700 | 0.114 | 0.413 | 0.127 | 0.396 |
| Exo S-40 | 0.903 | 0.805 | 1.118 | 0.935 | 0.733 | 0.615 | 0.630 | 1.132 | 0.459 | 1.410 | 0.765 | 0.599 | 1.890 | 0.717 |
| Exo S-50 | 0.908 | 0.856 | 1.082 | 0.832 | 0.774 | 0.581 | 1.068 | 1.007 | 0.451 | 1.369 | 0.297 | 0.611 | 1.756 | 0.688 |
| Exo S-141 | 0.955 | 0.776 | 1.113 | 0.844 | 0.752 | 0.713 | 0.937 | 0.970 | 0.447 | 1.422 | 0.341 | 0.649 | 1.974 | 0.643 |

[1]Data shown are absorbance readings at 405 nm taken from microtiter plates.

6. Identification of Adhesin Receptor Molecules

This section describes studies in which specific adhesin molecules were tested for their abilities to specifically bind to and discriminate between glycosphinogolipids.

A. Binding of *P. aeruginosa* and Exo S to GSLs

Methods for examining the binding of *P. aeruginosa* strain DG1 and Exo S derived from *P. aeruginosa* strain DG1 to GSLs on TLC plates, are described in Example 7A. Identities and locations of the GSLs to which bacteria or enzyme bind were determined by comparing sites of positive

TABLE 4

| $K_m$ Values for Binding to Asialo- and Mono-Sialo-GM1 | | |
|---|---|---|
| | Apparent $K_m$ of Binding to | |
| | Asialo-GM1 | Mono-sialo-GM1 |
| PAK Pili | 0.14 μg/ml | ND[1] |

TABLE 4-continued $K_m$ Values for Binding to
Asialo- and Mono-Sialo-GM1

| | Apparent $K_m$ of Binding to | |
|---|---|---|
| | Asialo-GM1 | Mono-sialo-GM1 |
| PAO Pili | $1.7 \times 10^{-2}$ | 15.65 µg/ml |
| Exo S | 1.29 µg/ml | ND |

[1]The affinity of PAK pili and Exo S for mono-sialo-GM1 was too low for a determination of the apparent $K_m$ of binding due to the low signal.

C. Binding of Pili to Oligosaccharides

Figure 7:
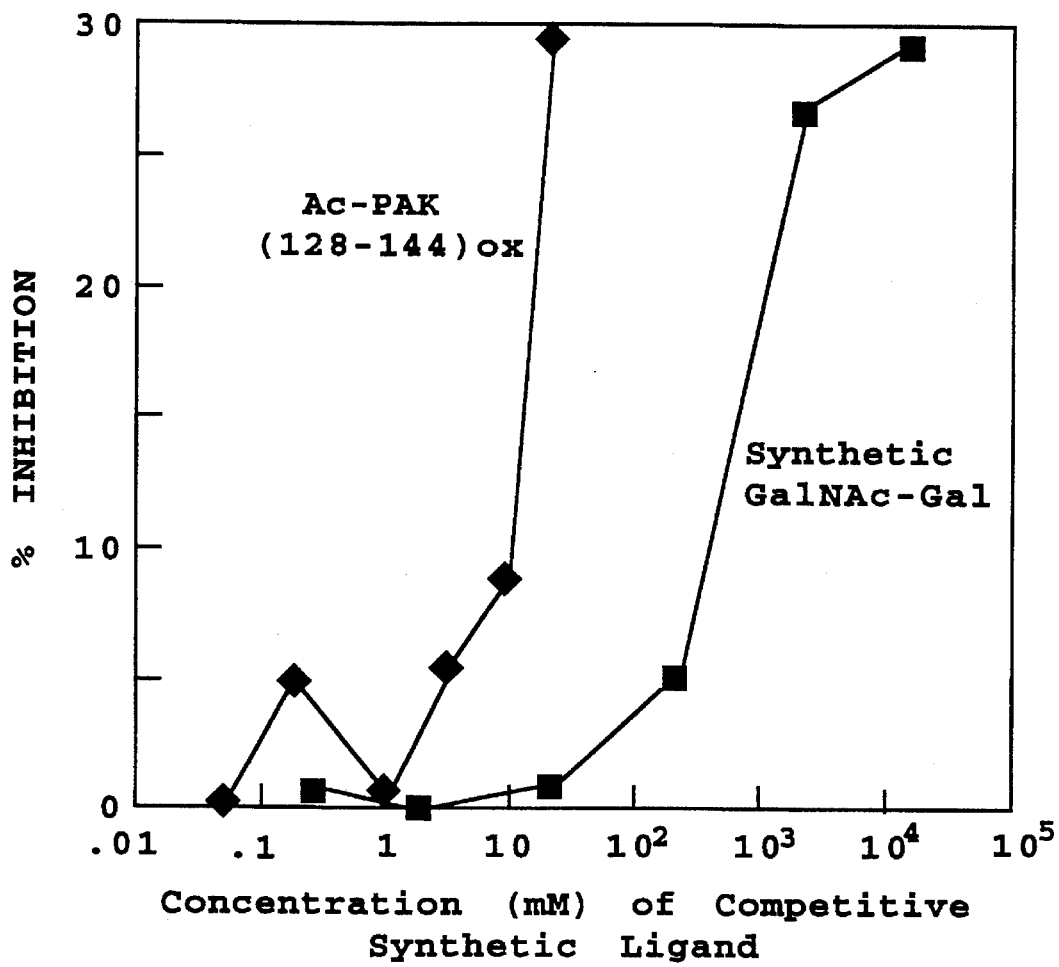
FIG. 7 shows a plot of the inhibition of binding of PAK pili to GalNAcGal-BSA by peptide Ac-PAK(128–144)ox (solid diamonds) and by GalNac-Gal (open squares)

Binding of purified pili to the sugar moieties representative of those present in reactive gangliosides was achieved by first conjugating the sugar moiety to bovine serum albumin (BSA), then adsorbing the BSA-conjugated sugar moiety to the wells of microtiter plates. FIG. 7 shows results of experiments wherein binding of PAK pili to immobilized βGalNAc1-4βGal-BSA was carried out in the presence of increasing concentrations of competitors PAK pilin derived peptide Ac-PAK(128–144)ox, comprising the 17 amino acid sequence of PAK pilin residues 128–144 having acetylated sulfhydryl groups (solid diamonds), and free disaccharide GalNAcGal. The ability of the synthetic peptide region of the pilin protein to effectively compete for binding to the substrate indicates that recognition of the immobilized disaccharide was effected at least in part by this region of the protein.

D. Binding of ExoS peptide to $GM_1$ and asialo-$GM_1$

Binding of Exo S peptide to monosialoganglioside $GM_1$ and asialoganglioside $GM_1$ was determined, according to methods detailed in Example 7, herein. Briefly, the gangliosides were coated onto the wells of microtiter plates and binding of biotin-exo S peptide biotin-G4-SEQ ID NO: 2 to the coated plates was determined in an ELISA format assay. Absorbance at 405 nm was recorded, with the results shown in Table 5 below. Titers against the gangliosides are shown for a biotin-exoS peptide solution having a concentration of 0.53 mg/ml.

TABLE 5

| Ganglioside | Titer |
|---|---|
| $GM_1$ | $10^{-3}$ |
| Asialo-$GM_1$ | $10^{-3}$ |

The reactivity of the Exo S peptide shown in the table above is similar to the reactivity in binding to $GM_1$ and asialo-$GM_1$ of several pilin peptides, including the peptide from *Pseudomonas aeruginosa* strain PAK and having the sequence SEQ ID NO: 5.

7. Inhibiting Bacterial Infections

As demonstrated above, antibodies produced against Exo S and particularly those showing activity in inhibiting the cytotoxic effects of Exo S, such as monoclonal antibody MCA1, are effective to inhibit adhesion of intact Pseudomonas cells to buccal epithelial cells. Antibodies produced against Exo S have been shown to be immunoreactive with pilin protein from a variety of *P. aeruginosa* strains (Table 2). More specifically, as described above, antibodies produced in response to the core Exo S peptide (SEQ ID NO: 2) are cross-reactive with pilin peptides from at least six different strains of Pseudomonas (Table 3, FIG. 8).

The invention thus includes, in another aspect, a method of blocking attachment to target epithelial cells, of organisms having surface proteins that are antigenically cross-reactive with antibodies produced against the bacterial toxin Exo S or a peptide derivative thereof. The method includes contacting the microorganism with antibodies produced against Exo S or Exo S peptide. Such antibodies may be referred to as binding/inhibitory antibodies, with reference to their abilities to bind to the cross-reactive surface protein and to block binding of the microorganism with target epithelial cells, such as BECs. Such contacting can occur as a result of production of such antibodies by immunization of an animal with a peptide or peptide conjugate, as described in Section 8, below, or by passive immunization of formed antibodies.

The peptide used to produce the binding inhibitory antibody is preferably selected from peptides containing epitopes formed by the sequence SEQ ID NO: 2 and having the characteristic of immunospecific binding to monoclonal antibody MCA1, as discussed in Sections 2 and 4.

Alternatively, the peptide used to produce the antibody is one selected for its cross-reactivity with antibodies produced to *P. aeruginosa* pilin, and particularly those antibodies, such as PK99H, directed to the C-terminal pilin peptide characterized as containing the binding epitope which recognizes target epithelial cells as described in Section 3.

The antibody, either polyclonal or monoclonal, may be generated by standard methods, such as those outlined in Section 3-B, above. One antibody useful in the method is the MCA1 monoclonal antibody described in Section 3-A. Other antibodies are the Exo S-peptide monoclonal antibodies (i.e., Exo S-28, Exo S-40, Exo S-50 and Exo S-141), produced in response to immunization with Exo S peptide (SEQ ID NO: 2), as described in Example 4.

In one embodiment, such an antibody is used therapeutically in a passive immunization protocol. In such a protocol, the antibody is administered to the infected subject. Example 8 describes results of studies in which binding/inhibitory antibody PK99H was effective to prevent infection of mice by *Pseudomonas aeruginosa*. In a therapeutic setting, for use in an infected human, the binding/inhibitory antibody may preferably be a chimeric antibody containing the variable region of a mouse monoclonal binding/inhibitory antibody, including mouse monoclonal anti-Exo S antibody MCA1, or any of the binding/inhibitory Exo S-peptide antibodies, and the constant region of a human immunoglobulin gene. Details of preparing such a chimeric antibody are available in the art. Alternatively, binding inhibitory antibodies may be produced in a subject by vaccinating the subject with a peptide containing the immunogenic region formed by the Exo S peptide sequence SEQ ID NO: 2, as described in Section 8.

Microorganisms which are responsive to such treatment can be readily identified by the methods described above, for example, by showing binding of antibodies prepared against Exo S peptide to the microorganism, or by showing cross-reactivity of isolated adhesins to the antibodies.

8. Vaccine Compositions

Also included in the invention is a vaccine composition containing an Exo S peptide and an immunogenic peptide carrier to which the peptide is bound. The composition is used as a vaccine against infection by microorganisms which have surface proteins which are antigenically cross-reactive with antibodies produced against a C-terminal portion of Exo S, and particularly the epitope formed by the sequence SEQ ID NO: 2 and characterized by (a) immunospecific binding to monoclonal antibody PK99H or MCA1; (b) a peptide length less than 20 amino acid residues; and (c) ability to block binding of *Pseudomonas aeruginosa* to buccal epithelial cells.

More particularly, in experiments carried out in support of the present invention and detailed in Example 8 herein, it has been found that the PAK pilin derived peptide having the sequence SEQ ID NO: 4, when conjugated to an appropriate carrier molecule, is effective to provide protection against infection by *Pseudomonas aeruginosa* in an in vivo model of infection. This peptide was described in co-pending, co-owned U.S. patent application U.S. Ser. No. 07/638,492 as comprising a core reactive region the pilin peptide, with respect to binding of pilin by monoclonal antibody PK99H. Similarly, protection was observed after immunization of mice with the peptide conjugate, comprising the peptide sequence of pilin peptide PAK(128–144)$_{ox}$ which includes the sequence SEQ ID NO: 4, flanked at either end by several amino acid residues.

According to the present invention, an Exo S peptide which is cross-reactive with monoclonal antibody PK99H and which elicits antibodies which bind to the region of Pseudomonas pilin which has been shown to be particularly reactive with antibody PK99H, is effective in a vaccine composition which is protective against Pseudomonas and immunologically related microorganisms (i.e., having cross-reactivity with a Pseudomonas pilin reactive antibody, such as monoclonal antibody PK99H). As shown herein, particularly in Table 3 and Section 5b, above, the Exo S peptide having the sequence SEQ ID NO: 2 fulfills these criteria. That is, this peptide elicits production of antibodies, such as monoclonal antibodies Exo S-28, Exo S-40, Exo S-50, and Exo S-141, which recognize PK-99H reactive regions of pilin derived from a number of strains of Pseudomonas, and it is reactive with monoclonal antibody PK99H.

Particularly useful immunogenic carriers include keyhole limpet hemocyanin (KLH), tetanus toxoid, poly-L-(LAS:GLUE), peanut agglutinin, poly-D-Lysine, diphtheria toxoid, ovalbumin, soybean agglutinin, bovine serum albumin (BSA), human serum albumin, and the like.

The peptide may be conjugated to the carrier by a variety of known methods, including chemical derivatization or by standard genetic engineering techniques known in the art (e.g., Ausubel, et al.).

Vaccines and inocula of the present invention may be administered by injection, usually intramuscularly or subcutaneously, orally by means of a enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the subject to be immunized, the carrier used, the adjuvant used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide. Generally, it is anticipated, based on animal studies, that an effective dose of such a peptide would produce in the subject an antibody titer of at least about 1/10,000.

9. Peptide Treatment

In one preferred mode of administration, peptides of the invention are delivered by nasal insufflation of powders or atomized solutions containing the peptide. This mode of administration has the advantage that delivery of the peptide is made directly to the pulmonary mucosal epithelial surface.

Yet another use of the peptides of the invention is as target molecules for drug delivery to pulmonary epithelial cells. Since the peptides bind specifically to epithelial cells, they are construed to be useful as therapeutic adjuvants in pathological conditions involving epithelial cells present in the lungs which are common targets of Pseudomonas and related pathogenic organisms. One such condition is carcinoma of the lung. In one preferred use, the peptides of the invention are conjugated to a photoactivatable chemotherapeutic agent useful in the treatment of lung carcinoma. The drug-peptide conjugate is then administered by nasal insufflation, and the drug is activated by high intensity light delivered through a bronchoscope.

The following examples illustrate methods for preparing and using the peptide and antibody of the invention. The examples are intended to illustrate, but not limit, the scope of the invention.

EXAMPLE 1

Purification of Exo S

Exo S was purified from *P. aeruginosa* strain DG1 by published methods (Woods, et al., 1987). The composition of the preparations used in the glycosphingolipid binding studies varied as some samples contained lipopolysaccharide. The preparation used in the adherence inhibition assays produced a single protein band on sodium dodecyl sulfate polyacrylamide gels (SDS-PAGE) as visualized by Coomassie blue staining.

EXAMPLE 2

DNA Sequence of Exo S

1. Cloning of Exo S

The gene for Exo S was cloned from *P. aeruginosa* strain DG1 using an oligonucleotide probe based on the partial N-terminal amino acid sequence to screen a library of DG1 SstI fragments inserted into PKT230 in *Escherichia coli* DH1 as described by Sokol, et al. (1990).

2. Sequencing of Structural Gene for Exo S

The *P. aeruginosa* Exo S structural gene was sequenced by the Sanger dideoxy-chain termination method (Sanger, et al.; Tabor, et al.) as modified by using the Sequenase Kit (U.S. Biochemical Corp., Cleveland, Ohio) as described by the manufacturer. Overlapping clones were generated by the method of Dale (Dale, et al.). Sequence data were analyzed by using International Biotechnology, Inc. software and the University of Wisconsin Computer Group Software (Devereux, et al.).

EXAMPLE 3

Solid-Phase Synthesis of Pilin PAK and Exo S Peptides

Abbreviations used in this example are BOC, tertiary butoxycarbonyl; DCM, dichloromethane; TFA, trifluoroacetic acid; and BOC-AA-OH, amino acids protected at the alpha amino group by BOC group.

Commercially available phenylacetamidomethyl resin for polypeptide synthesis is obtained from Applied Biosystems, Inc. (Foster City, Calif.). BOC-AA-OH were obtained from Institute Armand Frappier (Laval, Quebec, Canada). Side-chain protecting groups on the residues are as follows: o-(p-bromobenzoyloxycarbonyl) for tyrosine, o-benzyl for threonine, serine, aspartic acid and glutamic acid; S-methoxy-benzyl for cysteine, 2-chlorobenzyloxycarbonxyl for lysine and formyl tryptophane.

1. Solid-Phase Synthesis

In preparing a synthetic polypeptide of this invention by the above-phase method, the amino acid residues are linked to a resin (solid-phase) through an ester linkage from the carboxy-terminal residue.

Reactive amino acid side chains are also protected during synthesis of the polypeptide. Couplings are typically carried out using a 2-fold molar excess of protected amino acid and one equivalent of dicyclohexyl carbodiimide over the number of milliequivalents of initial N-terminal amino acid. For asparagine (N) and glutamine (Q), 2 molar equivalents of N-hydroxybenzotriazole and dicyclohexyl carbodiimide were used. Coupling reactions are monitored by a ninhydrin reaction test known in the art and are typically more than 99% complete.

2. Oxidation and Purification of the Peptide

The peptide is cleaved from the resin and subsequently cyclized to form a disulfide bond. The cleavage of the peptide and the complete removal of the side-chain protecting groups is accomplished using anhydrous hydrogen fluoride. The resin is suspended in a mixture containing hydrogen fluoride and anisole (9:1, v/v) and the reaction is allowed to proceed in vacuo for 45 minutes at 5° C. The hydrogen fluoride is then evaporated. The resin is removed and washed with ether (3×10 ml) and the peptide is extracted with 30% acetic acid (3×10 ml). The combined filtrates are diluted to give a 5% aqueous acetic acid solution and lyophilized.

The crude peptide can be purified on an analytical reversed-phase HPLC column (250×4.6 mm internal diameter) using a shallow gradient. The crude peptide is dissolved in the smallest volume of starting buffer possible (about 5 ml). The highly concentrated peptide is centrifuged to sediment undissolved material. An analytical sample, 5–10 μl, is chromatographed using a linear gradient (solvent A is 0.05% aqueous TFA and solvent B is 0.05% TFA in acetonitrile) to determine the total amount of peptide present. When the crude peptide contained hydrophilic and hydrophobic impurities with retention times close to that of the peptide of interest in the analytical run (1% B/min gradient rate), a shallow gradient of 0.2% B/min with a flow rate of 1 ml/min is employed.

The whole stock solution of 30–50 mg is injected onto the column and the run is monitored at 210 nm. Fractions (1 ml) are collected and analyzed. Every third or fifth fraction is analyzed to identify the region on the chromatogram with the peak of interest. Further analysis of the fractions within this region are then carried out. The chromatogram of each run can be compared with the initial analytical run prior to purification to ascertain the peak of interest. In this way, the shoulders of the neighboring peaks are eliminated, while fractions of interest are pooled and freeze-dried. Dried peptides are stored in glass vials in a desiccator.

Mass spectrometry and HPLC analysis are used to confirm the peptide structure.

EXAMPLE 4

Preparation of Antibodies

A. Polyclonal Antibodies

Polyclonal antiserum to Exo S (anti-Exo S) was raised in New Zealand rabbits was prepared as described previously (Woods, et al., 1987). Western blotting with this antibody preparation revealed activity with Exo S and LPS. Therefore, antiserum used in gold labeling studies was absorbed with *P. aeruginosa* strain DG-ExS5, which is deficient in the production of Exo S (Woods, et al., 1985).

Polyclonal antiserum to PAK pili (anti-PAK) were prepared essentially as described above, using an antigen pili isolated from *P. aeruginosa* strain PAK, isolated as described by Paranchych, et al. (1979). Polyclonal antiserum to a specific sequence of PAK pilin protein (amino acid residues 128–144 of the purified protein; anti-PAK(128–144)$_{ox}$) was prepared using the peptide conjugated to keyhole limpet hemocyanin as described in a previous publication (Lee, et al., 1989).

B. Monoclonal Antibodies

1. Anti-pilus antibodies

Monoclonal antibodies against native PAK pili protein were prepared according to methods described elsewhere by the inventors (Doig, et al., 1990). BALB/c mice were immunized four times at 1 week intervals, by intraperitoneal injection of 100 micrograms of PAK pili in 0.5 ml phosphate buffered saline (PBS) supplemented with 0.1% (wt/vol) Al(OH)$_3$. The mice were not given further immunizations for 4 weeks following the initial immunization period. The mice were then further immunized by intraperitoneal injection of 100 μg of PAK per mouse in 0.5 ml PBS, at one week intervals, for an additional 4 week period. A final intravenous injection of PAK pili (5 μg/mouse) was given. BALB/c mice were immunized with weekly injections of PAK pili, which were isolated as described by Paranchych, et al. (1979). Spleen cells from the animals were fused with mouse myeloma cell line NS1 (Irvin, et al., 1985), and successful fusions were screened by an ELISA method for ability to secrete anti-pilin antibody. A library of 262 hybridoma clones that secreted antibodies immunoreactive with PAK pili were obtained. Protein A purified Mabs were then screened against pilin peptide fragments (Doig, et al., 1985), to determine specificities of these antibodies. Four hybridoma cell lines were selected for further specificity studies: cell lines PK99H, PH34C, PK3B, and PK41C.

Four days following the final injection, mouse spleens were removed, and the spleen cells were collected. Spleen cells were fused with mouse NS1 myeloma cells (ATCC TIB 18) at a ratio of 10:1 (spleen: myeloma) with 45% polyethylene glycol (MW 1000; Sigma, St. Louis, Mo.) according to standard methods (Kennett, 1980, in Monoclonal Antibodies. edited by Kennett, R. H. et al. Plenum Press, NY). Fused cells were allowed to recover for 24 hours in DME medium (Gibco) supplemented with 20% fetal calf serum, 2 mM L-glutamine. Cells were recovered by centrifugation, resuspended in HAT medium (Flow Laboratories, Mississauga, Ontario, Canada) and transferred into microtiter dishes at a density of about $10^4$ myeloma cells per well of 96-well microtiter plates containing a feeder layer of CAF$_1$ mouse peritoneal macrophages ($10^3$/well).

The tissue culture supernatant fluids from each microtiter well were then tested for the presence of antibody to PAK pili by an ELISA utilizing purified PAK pili (10–50 μg/well) as solid phase, according to published procedures (Doig, et al. 1990, Infect. Immun. 58: 124–130). Out of approximately 720 wells, approximately 540 cultures contained successful fusions. Of these, 262 cultures showed specific immunoreactivity with PAK pili. Clones were selected from these cultures for further study.

The selected hybridoma clonal cell lines producing monoclonal antibodies to PAK pili were scaled up into 5 ml DME medium supplemented with 20% fetal calf serum, 2 mM glutamine, hypoxanthine, aminopterin and thymidine (HAT media). Clones were frozen and subsequently subcloned in semisolid agarose to ensure that multiple antibodies were not generated. Hybridoma cell lines were amplified by ascites tumor induction in pristane primed mice, according to standard methods, and purified antibodies were characterized.

For some experiments, Fab fragments were prepared, using immobilized papain (Pierce Chemical Co.), according to manufacturer's instructions and standard procedures described in a published article (Doig, et al. 1990, Infect. Immun. 58: 124–130).

Immunoblots of purified PAK and PAO pili revealed that monoclonal antibodies identified as PK99H and PK3H were specific for PAK pilin protein, while PK34C and PK41C Mabs were immunoreactive with both PAK and PAO pilin peptide. PK99H and PK34C Mabs were both immunoreactive with a C-terminal fragment of PAK pilin. Hybridoma cell lines PK99H and PK34C (Doig, et al., 1985) were deposited in the cell depository of the Department of Medical Microbiology and Infectious Diseases of the University of Alberta, Alberta, Canada, and are identified by cell lines Nos. PK99H and PK34C.

2. Anti-Exo S antibodies

Monoclonal antibodies to purified Exo S protein were prepared essentially as described by Woods, et al., (1987), as follows: A purified preparation of Exo S was subjected to dialysis against 1% formalin in 0.1M Tris buffer (pH 8.0) and 0.2M L-lysine, followed by dialysis against 0.2M L-lysine in 0.95% NaCl, pH 6.3. BALB/c mice were injected intraperitoneally four times with 50 µg of the formalin-lysine treated Exo S on days 0, 7, 14, and 21.

Three days after the final injections, spleens were removed, and the spleen cells were collected. Spleen cells were fused with NS-1 myeloma cells (ATCC TIB 18) at a ratio of 10:1 (spleen: myeloma) with 50% polyethylene glycol (MW 1500). Fused cells were transferred into microtiter dishes at a density of $6 \times 10^4$ input spleen cells per well and maintained for 14 days in HAT medium (Flow Laboratories, Mississauga, Ontario, Canada). The tissue culture supernatant fluids from each microtiter well were then tested for the presence of antibody to exo S by an ELISA utilizing purified exo S (10 micrograms/well) as solid phase. Out of approximately 1000 wells, 200–300 wells contained successful fusions. Of these, 20–30 cultures showed specific immunoreactivity with exo S protein.

Hybridoma cell lines producing monoclonal antibodies to exo S were transferred to HT medium (Flow Laboratories) and cloned by limiting dilution. The hybridoma cell lines were extensively subcloned six times to ensure that multiple antibodies were not generated. Hybridoma cell lines identified as anti-exo S MCA were amplified by ascites tumor induction in pristane primed mice, according to standard methods. Antibodies present in ascitic fluid were purified on hydroxylapatite column, and immunoreactivity was verified using Western blots.

Monoclonal antibodies to Exo S were additionally tested for ability to (a) inhibit enzyme (ADP ribosylation) activity and (b) neutralize cytotoxic effects of Exo S, as described by Woods, et al. (1987). Monoclonal antibody MCA1 was found to have relatively low potency in neutralization of cytotoxicity by Exo S. Monoclonal antibody MCA2 was found to have much greater potency in neutralizing the cytotoxic effects of Exo S. MCA2 was subsequently used in purification of the protein (Woods, et al., 1987). Monoclonal antibody MCA3 was shown to neutralize cytotoxicity but not inhibit enzyme activity.

3. Anti-Exo S peptide antibodies

Anti-Exo S peptide antibodies were prepared according to the protocol described in part A, above, using as antigen a conjugate of Exo S peptide having the sequence SEQ ID NO: 2 and tetanus toxin (TT). Six Balb C mice were immunized intraperitoneally with 10 µg each of antigen in adjuvant, weekly for four weeks. Sera were tested for immunoreactivity. Titers are reported in Table 6, below, are estimated from reactivity in a plate ELISA assay, using as solid phase reactive species, the Exo S peptide-TT conjugate.

TABLE 6

Polyclonal Titer of Mice Immunized with Exo-S Peptide

| Antigen | Titer | | |
|---|---|---|---|
| Exo S (native) | $>10^8$ | PAO Pili | $10_3$ |
| Exo S-BSA | $>10^8$ | PAO-BSA | $10^4$ |
| PAK pili | $10^4$ | KB7 pili | $10^4$ |
| PAK BSA | $10^4$ | KB7-BSA | $10^6$ |
| K122-4 pili | $10^4$ | | |
| K122-4-BSA | $10^6$ | | |

Spleens from three animals were pooled, and processed to produce cells for fusion with myeloma cells, as detailed in part B, above. Hybridoma supernatants were tested for presence of antibodies immunoreactive by ELISA test with the antigen. At least 141 positive clones were detected in the fusion of three spleens. Four clones of interest were further subcloned and deposited in the cell depository of the Department of Medical and Infectious Diseases of the University of Alberta, Alberta, Canada. These clones are identified by cell lines Nos. Exo S-28, Exo S-40, Exo S-50, and Exo S-141. Supernatants from the clones were tested for immunoreactivity with Pseudomonas derived antigens, as shown in Table 3.

4. Immunogold Labeling and Immuno-Electron Microscopy of PS Strain DG1

The antibody-gold-conjugate labelling procedure used was a modification of that described by Godfrey. Formvar coated electron microscope grids were coated with 0.1% bovine serum albumin in distilled water. A 5 µl suspension of PS strain DG1 was placed on the grids and allowed to settle for 5 minutes. Excess bacterial suspension was drained from the grids, and the grids were immediately floated over a drop of a solution containing a 1:10 dilution of anti-Exo S monoclonal antibody in PBS and incubated in 37° C. for 30 minutes. The grids were then washed three times by successive floating over drops of PBS (5 minutes each wash). The grids were then floated over a drop of anti-rabbit antibody gold conjugate (Sigma Chemical Co., St. Louis, Mo.) and incubated at 37° C. for 30 minutes. The grids were washed again as above, briefly rinsed in distilled water and examined (unstained) in a Phillips EM400 electron microscope.

FIGS. 2A and 2B show immunoelectron microscopy of *P. aeruginosa* cells exposed to monoclonal antibody raised against purified Exo S (2A) or phosphate buffered saline (2B) followed by exposure to protein A-colloidal gold.

EXAMPLE 5

Binding to Buccal Epithelial Cells

1. Preparation of Buccal Epithelial Cells

Buccal Epithelial Cells (BECs) were collected from ten healthy non-smoking male volunteers via wooden application sticks rubbed gently on the inside of cheeks, three wooden application sticks per cheek. These sticks were rubbed gently together in 30 mL phosphate buffered saline to suspend the BECs. These cells were washed three times with 30 mL phosphate buffered saline by successive centrifugation (650×g) and resuspended. The final pellet was suspended in 5 Ml phosphate buffered saline at Ph 7.2. This suspension was filtered (prewetted 70 μm nylon mesh) and the cells were diluted to a final concentration of 2×10$^5$ cells/Ml in phosphate buffered saline at Ph 7.2. This suspension was stored at 4° C. until ready for use.

2. Inhibition of Bacterial Adherence to BECs

The ability of purified Exo S, purified pili, and monoclonal antibodies to Exo S to inhibit binding of intact *P. aeruginosa* to buccal epithelial cells was examined essentially as described by Woods, et al. (1980). BECs (1.0 ml at 2.0×10$^5$ cells per ml) were incubated with the test agent at 37° C. prior to addition of an equal volume of $^{35}$S-labeled bacteria (*P. aeruginosa* strain DG1), suspended in PBS in a 15-ml polystyrene test tube, so that the final ratio of bacterial cells to BECs was about 1000:1. Incubation was carried out at 37° C. for 2 hours, with shaking. The cells were washed, filtered, and the filters were assayed for the presence of bound bacteria. Epithelial cells with bound bacteria were then collected by filtration on 12.0-μm-pore-size polycarbonate filters (Nucleopore Corp., Pleasanton, Calif.) that had been pretreated with 2% (wt/vol) bovine serum albumin in PBS to reduce nonspecific binding, washed with 15 ml of PBS, and then dried in scintillation vials. Aquasol (5 ml) was added to each vial, and the amount of radioactivity was determined by scintillation counting in a Beckman LS-150 liquid scintillation counter. All binding assays were performed in triplicate. Binding of bacteria to epithelial cells was corrected for nonspecific binding of bacteria to the 1.2-μm-pore-size filter (nonspecific binding was generally less than 15% of the experimental value). Epithelial cell concentration was determined at the end of the assay to correct for total cells present in the assay. Monoclonal antibodies PK34C and PK99H ($F_{ab}$ fragments) were effective inhibitors of binding of Pseudomonas to BECs, in the assay described above.

3. Inhibition of Binding of Pili to Becs

A. Preparation of $F_{ab}$ Fragments $F_{ab}$ fragments of the PK99H and PK3B monoclonal antibodies, described above, and non-immune IgG were prepared using immobilized papain (Pierce Chemical Co., Rockford, Ill.). Briefly, affinity purified antibody was dialyzed against 20 Mm cysteine Hcl, 10 Mm tetrasodium ethylenediaminetetraacetic acid (EDTA) in 20 Mm sodium phosphate buffer at Ph 6.2. Antibody (1 ml containing approximately 2 mg antibody) was added to 0.5 ml immobilized papain and incubated at 37° C. for 20 hours with shaking at 150 rpm. The immobilized papain was removed by centrifugation and the supernatant containing the Fab fragments was diluted with 1 ml of PBS.

The Fab fragments were purified by HPLC using a Protein G column eluted with PBS. Fab fragments were collected in the flowthrough, and Fc fragments were eluted from the column with 10 Mm glycine at Ph 2.75. Fab fragments were concentrated by placing the Fab effluent in dialysis tubing (molecular weight cutoff of <8000) and extracting liquid from the dialysis sack using polyethylene glycol (molecular weight of 15,000–20,000). The fragments were then dialyzed against PBS. Activity of Fab fragments was checked by ELISA and production of Fab fragments was confirmed by SDS-PAGE.

B. Preparation of PAK pili binding mixtures

PAK pili were isolated according to published procedures (Paranchych, et al., 1979). Fab fragments of antibodies PK99H and PK3B, prepared as described above, were preincubated with PAK pili. The final concentration of PAK pili was 5 μg/ml. Pili binding was detected using monoclonal antibody PK3B (which is specific against pilin protein, but not the PAK peptide). All Fabs were diluted such that their final titer as measured by ELISA to PAK pili was 10$^{-3}$.

C. BEC Binding Assay

Fab fragments were prepared from test antibody preparations for use in an assay to assess ability of antibodies to interfere with binding of PAK pili to buccal epithelial cells (BECs). Fab fragments (0.1 ml of 400–800 μg/ml) were added to an equal volume of PAK pili (20 μg/ml) in PBS, and were incubated for 30 minutes at room temperature. BECs (0.2 ml at 2×10$^5$ BECs/ml) were then added, and the mixture was incubated. Binding of pili to BECs was determined according to procedures detailed in a published article (Doig, et al. 1990, Infect. Immun. 58: 124–130), and inhibition of binding was measured.

EXAMPLE 6

Antibody Cross-Reactivity

1. Direct ELISA Experiments

Antigens were coated on NUNC 96-well polystyrene wells. Antigen (10 mg/Ml in 0.01M carbonate buffer, Ph 9.5) was added to each well (100 μl/well) and left for 6 hours at room temperature. Wells were then washed 3 times with 250 μl of PBS Ph 7.4 supplemented with 0.02% (wt/vol) BSA (buffer A). Wells were blocked with 5% (wt/vol) BSA in PBS pH 7.4 overnight at 4° C. Wells were washed three times and 100 μl of primary antibody was added for 2 hours. Each well was then washed 3 times with 250 μl buffer A using aspiration. A goat anti-mouse IgG (H+L) immunoglobulin-horse radish peroxidase conjugate (Jackson Laboratories, Bar Harbor, Me.) in buffer A (100 μl/well) was added and incubated for 2 hours at room temperature. The wells were washed 3 times with buffer A and 350 51/well substrate solution (1 mM 2,2'-azino-di-(3-ethylbenzthiazoline sulfonic acid), 0.03% (vol/vol) hydrogen peroxide in 10 mM sodium citrate buffer at pH 4.2) added. The reaction was stopped by the addition of 250 μl/well of 4 mM sodium azide and absorbance at 405 nm determined using an EL-407 plate reader.

Table 2 shows results of experiments using test antigens pili from *P. aeruginosa* strains PAK, PAO, and P1, as well as Exo S (Exo S) and the PAK pilus peptide PAK (128–144)$_{ox}$. Serial dilutions of test monoclonal or polyclonal antibodies prepared against pili, specific peptides of pili, or Exo S were tested for binding to these antigens. Reciprocals of the titers shown in Table 2 indicate the highest dilution of test antibody solution at which binding to the antigen in the plate was detected.

2. Competitive ELISA Experiments

Competitor and antibody were mixed together in 10 mM PBS pH 7.2 buffer containing 0.05% (w/v) BSA and incubated for 30 minutes at room temperature. The conditions of the assay were such that less than 50% of the antigen immobilized on the ELISA plate surface would be bound with antibody if there was no competitor present. The mixture of antibody and competitor was then added to wells (100 μl/well) coated with PAK pili fimbriae and blocked with BSA as described above. The ELISA was then performed as described above.

Figure 5:
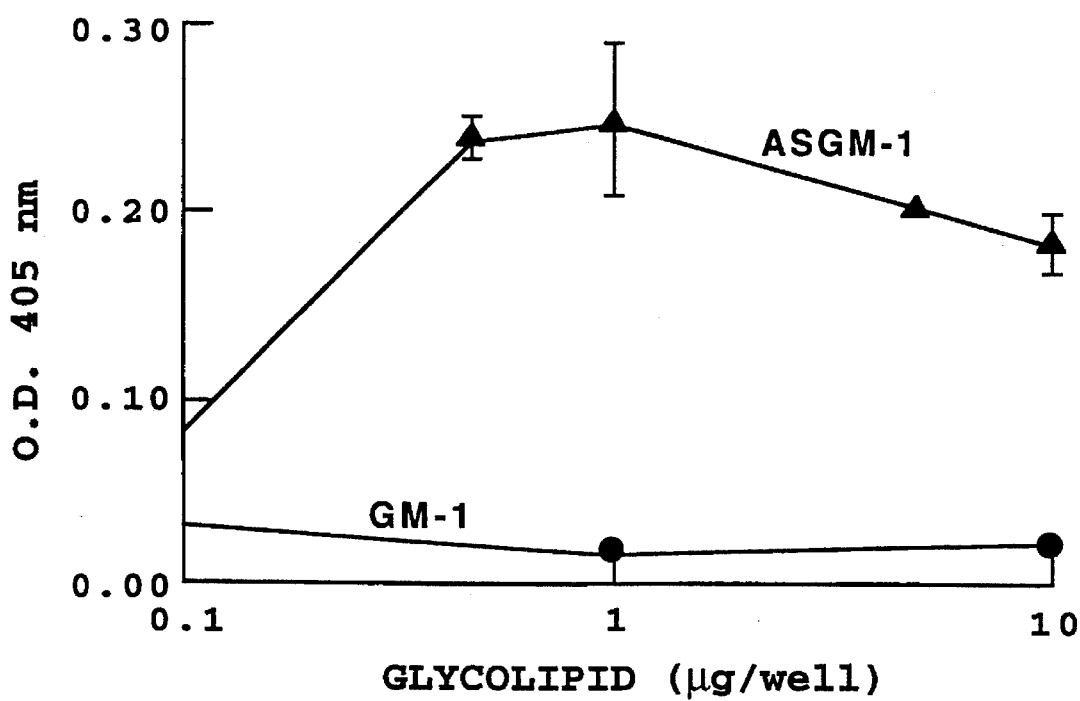
FIG. 5 shows a binding of purified Exo S to glycosphingolipids.
Figure 4B:
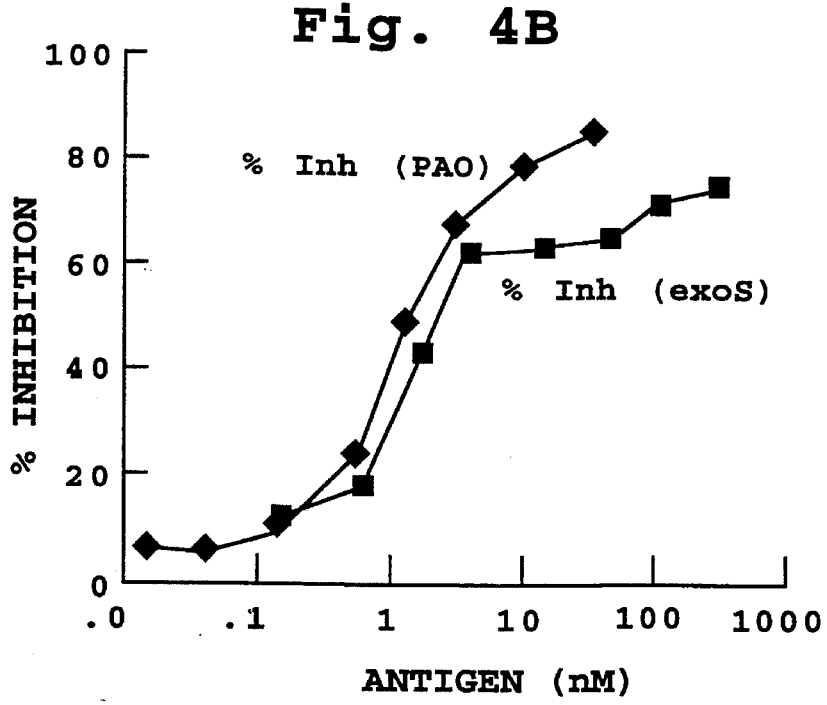

FIGS. 4A, 4B and 5 show the results of experiments in which PAK pili, PAO pili, or Exo S were coated onto ELISA plates at a concentration of 1 μg/ml. Wells were then blocked with excess non-reactive protein solution and washed to remove unbound materials. Polyclonal anti-Exo S antibody (Woods, et al., 1987) was then added to the wells. Competition between test agent and the anti-Exo S antibody was effected by pre-mixing the test agent and the antibody for 30 minutes at room temperature prior to adding the mixture to the antigen coated wells. After incubation of the anti-Exo S in the presence of test agent in the coated wells, the plates were washed, then reacted with alkaline phosphatase-linked second antibody, to quantitate binding of anti-Exo S to the coated wells.

3. Binding of ExoS peptide to PK99H Antibody

ExoS peptide was biotinylated such that the final sequence was: biotin-(G)$_4$-SEQ ID NO: 2. The peptide was synthesized by the solid-phase method described in Example 3, oxidized to form the disulfide peptide, and suspended in buffer to a final concentration of 0.53 mg/ml.

PK99H Monoclonal antibody was prepared against *P. aeruginosa* pilin protein, as described in co-owned U.S. patent application for "Pseudomonas Peptide Composition and Method", Ser. No. 07/638,492, filed Jan. 4, 1991. The antibody was purified from mouse ascites fluid by Protein G affinity high performance liquid chromatography.

The PK99H antibody was coated onto the wells of microtiter plates at a coating concentration of 5 ug/ml. Stock solutions of the antibody were diluted with 10 mM carbonate coating buffer, pH 9.6. Aliquots of 100 ul of the antibody solution were added to the wells and the microtiter plate was incubated overnight at 4° C.

Excess unbound antibody was aspirated and removed by washing the wells with Buffer A (10 mM phosphate, pH 7.4, containing 150 mM sodium chloride and 0.05% [wt/wt] BSA). The excess sites on the wells were then blocked with a 5% BSA solution. The biotin-exoS peptide was serially diluted (10-fold) and 100 ul aliquots, in triplicates, were added to the wells. The dilutions were made using Buffer A. The microtiter plate was then incubated for an hour in an oven set at 37° C. The wells were washed (5x) with Buffer A. Aliquots of 100 ul of a strepavidin-alkaline phosphatase solution (1:2500) were added to the wells and incubated for an hour in an oven set at 37° C.

The wells were washed (5x) with Buffer A. The substrate for the alkaline phosphatase, p-nitrophenylphosphate (1 mg/ml in substrate buffer), was added to the wells (100 ul/well) and the absorbance at 405 nm was recorded. The biotin-ExoS peptide solution bound to the immobilized PK99H monoclonal antibody, with an end-point titer of the solution of about $10^{-4}$.

EXAMPLE 7

Binding to Glycosphingolipids

1. Glycosphingolipids Thin Layer Chromatography (TLC) Binding Assay

Purified glycosphingolipids (GSLs) were purchased from Sigma Chemical Co. The total non-acid glycosphingolipid fraction from dog intestinal mucosa, a gift from G. Hansson, University of Goteborg, Goteborg, Sweden, was described previously (Hansson, et al., 1983). The TLC plate binding assay was carried out using standard methods known in the art.

Glycosphingolipids (ganglio-tetraosyl ceramide), $GM_1$, and neutral GSLs of dog mucosa were separated on aluminum-backed silica gel Si50 HPTLC plates in chloroform-methanol-water (60:35:8). One plate was sprayed with cupric acetate for chemical detection and duplicate plates were used for bacterial or Exo S binding assays. The TLC plates were immersed in 0.3% polyisobutylmethacrylate in diethylether-hexane (1:1) for 1 minute and air dried. Plates were wet with phosphate buffered saline (PBS) containing 0.2% Tween™ (PBS-T) and overlaid with 2 to 3 ml of Exo S diluted in PBS-T or a suspension of *P. aeruginosa* strain DG1 diluted to O.D.$_{600}$ of 0.5 in PBS-T. After a 2 hour incubation at room temperature, the plates were washed 5 to 6 times with PBS-T. After the final incubation, the plates were washed 3 times with PBS-T and 2 times with 0.05M Tris-saline, pH 7.4. The plates were developed by immersion in Tris-saline containing 2 mg of Fast Red and 1 mg of naphthol phosphate per ml. Plates were observed for development of a red precipitate (FIG. 6).

2. Solid Phase Binding Assay

A. Binding of Exo S to GSLs

Glycosphingolipids were diluted in methanol, and 25 µl aliquots were added to individual wells of 96-well microtiter plates. The plates were dried slowly overnight at room temperature, rinsed once with PBS-T, and 50 µl of test agent diluted in PBS was added to each well (10 µg protein/well). The plates were incubated for 2 hours at room temperature and rinsed 4 to 5 times with PBS. Bound Exo S was detected by sequential addition of 50 µl of anti-Exo S and alkaline phosphatase-conjugated goat-anti-rabbit IgG with intermittent and final washes with PBS-T. The plates were developed by addition of 100 µl of 1 mg of nitrophenol phosphate in 10% diethanolamine buffer (pH 9.6). The plates were read at 405 nm. (FIG. 8 shows Exo S as test agent; FIGS. 9A–9D and FIG. 10 show the results of studies in which PAK pili were tested for immunoreactivity; Table 4 summarizes these data.)

B. Binding of Pili to GSLs

The binding of PAK Pili, PAO pili and Exo S to the glycolipids asialo-GM1 and GM1 was determined by a modified ELISA type assay. The glycolipid (after purity was verified by TLC analysis with authentic standards) was coated on ELISA plates by dissolving the glycolipids in 10% (v/v) chloroform in methanol to a concentration of 1 mg/ml and diluting the glycolipids in methanol to obtain the appropriate concentration, a 100 µl of the glycolipids in methanol to each well and allowed to evaporate to dryness at 4° C. The wells were then blocked by the addition of 100 µl/well of 5% (w/v) BSA in PBS pH 7.2 for 1 hour at 37° C. Wells were washed 5 times with 250 µl/well of 0.05% (w/v) BSA in PBS (pH 7.2). Pili or Exo S in 0.5% (w/v) BSA in PBS pH 7.2 were then added (100 µg/well) and incubated for 1 hour at 37° C. Wells were then washed 5 times with 350 µl/well of 0.5% (w/v) BSA in PBS (pH 7.2). The appropriate antibody (PK3B for PAK pili, polyclonal anti-PAO pili for PAO pili, and polyclonal anti-exoenzyme S antibody for Exo S) was then added (100 µl/well) and incubated to 37° C. for 1 hour. Wells were then washed 5 times with 250 µl/well antibody-enzyme conjugate (anti-mouse IgG-HRP conjugate for PK3B and anti-rabbit IgG-alkaline phosphatase conjugate for the polyclonal antibodies). Wells were then washed 5 times with 250 µl/well of 0.05% (w/v) BSA in PBS (pH 7.2). The appropriate substrate was then added and the optical density at 405 nm was then determined after the reaction had been stopped.

C. Binding of ExoS peptide to $GM_1$ and asialo-$GM_1$

Monosialoganglioside $GM_1$ and asialoganglioside $GM_1$ were coated onto the wells of microtiter plates and the gangliosides were diluted with methanol to a coating concentration of 5 ug/ml. The methanol was allowed to evaporate off and the wells were blocked with a 5% bovine serum albumin solution.

The biotin-exo S peptide described in Example 6.3, above, was serially diluted (10-fold) and triplicates of 100 ul aliquots were added to wells coated with GM1 and asialo-GM$_1$. Dilutions were made using buffer A (10 mM phosphate, pH 7.4, containing 150 mM sodium and 0.05% [wt/wt] BSA). The microtiter plate was incubated for an hour in a 37° C. oven.

The wells were washed (5×) with Buffer A. Aliquots of 100 ul of a strepavidin-alkaline phosphatase (1:2500) solution were added to the wells and the incubation at 37° C. was repeated.

The wells were washed (5×) with Buffer A. The enzyme substrate, p-nitrophenylphosphate (1 mg/ml in substrate buffer; Sigma, St. Louis, Mo.), was added to the wells (100 ul/well) and the absorbance at 405 nm was recorded.

3. Inhibition of PAK Pili Binding to GalNacGal-BSA

Test agents were tested for ability to inhibit binding to GSL conjugated to bovine serum albumin (BSA).

EXAMPLE 8

In Vivo Protection from Infection by *Pseudomonas aeruginosa*

A. Inhibition of *P. aeruginosa* infection in vivo by PK99H Antibody

Groups of 8 AB.Y mice were passively immunized by intraperitoneal (IP) administration of 0.5 mg/0.1 ml of monoclonal antibody PK99H in phosphate buffered saline pH 7.2 or 0.1 ml of phosphate buffered saline as a control and then challenged 20 hours later with *Pseudomonas aeruginosa* strain K. When the challenge dose was 10 times the lethal dose-50 (LD$_{50}$), 50% of the animals survived, while with a challenge dose of 5 times the LD$_{50}$, 100% of the animals survived the challenge. With both the 5 times and the 10 times LD$_{50}$ challenge dose, 100% of the control animals succumbed to the infection. The monoclonal antibody PK 99H thus confered substantial protection to mice from subsequent infection with viable *P. aeruginosa* cells.

B. Inhibition of *P. aeruginosa* infection by Pilin Peptide Conjugate

Pilin peptide containing the core peptide sequence D-E-F-I-P-K was coupled photochemically to the carrier VP6 (a recombinant rotavirus nucleocapsid viral particle) by its N-terminus with benzoylbenzoic acid coupled to norleucine and a diglycine spacer. The peptide conjugate was utilized to immunize 8 AB.Y mice by injecting 50 μg of conjugate subcutaneously (SC), employing alum as an adjuvant in phosphate buffered saline (pH 7.2) at week 0, week 2 and week 4. Control mice were given either phosphate buffered saline (pH 7.2) (2 mice), 2% alum (2 mice), or VP6 in 2% alum (50 μg/injection, 8 mice) at week 0, week 2 and week 4. The mice were subsequently challenged at week 6 by administration of 8.7×10$^5$ CFU of *Pseudomonas aeruginosa* strain K. All control animals died from the subsequent *P. aeruginosa* infection while 7 of 8 mice immunized with the SEQ ID NO: 4-VP6 conjugate survived.

High survival rates were also observed when animals were protected with a pilin peptide having the core peptide sequence SEQ ID NO: 4, flanking sequences of 1–5 amino acids, and attachment of each peptide end to a KLH carrier protein. High survival rates are also observed with animals protected by immunization with a pilin peptide sequence of PAK(128–144)$_{ox}$ (which is conformationally constrained by a disulfide bridge) is coupled to tetanus toxoid.

EXAMPLE 9

Inhibition of ADP-ribosyl Transferase Activity

Crude extracts containing aminoacyl transferase factors were prepared from wheat germ as described by Chung and Collier (Infect. Immun. 16: 832–841). ADP-ribosyl transferase activity was measured by the incorporation of radioactivity from [adenine-$^{14}$C]NAD$^+$ trichloroacetic acid-precipitable material in the presence of crude wheat germ extracts. Unless otherwise noted, the reaction was performed at 25° C. for 30 minutes in 0.1 ml of 50 mM dithio-threitol-0.12 mM [adenine-$^{14}$C]NAD$^+$ (10.6 mCi/mmol; Amersham Corporation (Arlington Heights, Ill.), wheat germ extract containing 150 to 160 μg of proteins, and various amounts of exoenzyme S. The reaction was stopped by the addition of 0.1 ml of 10% trichloroacetic acid, and the precipitates were collected, washed, and counted as previously described (10). One unit of enzyme activity was defined as that amount of enzyme which transferred 4.0 nmol of [adenine-$^{14}$C] ADP-ribose per min from [adenine-$^{14}$C]NAD$^+$ into trichloroacetic acid-precipitable material in the presence of crude wheat germ extracts. In additional experiments, purified oubain-sensitive ATPase obtained from Sigma Chemical Co. (St. Louis, Mo.) was substituted for wheat germ extract as the substrate (25). Monoclonal antibodies to exo S were tested for their ability to inactivate ADP-ribosyl transferase (ART) activity by measuring enzyme activity after incubation with 0.2 mg of purified exo S. This concentration of exo S gave appproximately 50% maximum activity in the ADP-ribosyl transferase assay. Normal mouse serum and rabbit anti-toxin A antiserum were used as controls. Monoclonal antibody and control serum preparations were adjusted to 100 micrograms of IgG or IgM per milliliter and serially diluted in saline containing 0.1 mg of bovine serum albumin. After preincubation with exo S for 15 min at 37 degrees, the mixtures were assayed for ADP-ribosyl transferase activity. The highest dilution of each monoclonal antibody preparation which gave less than 50% of control (normal mouse serum) values in the ADP-ribosyl transferase assay was taken as the endpoint.

Table 7 shows a comparison of monoclonal antibodies derived from hybridomas produced in one exemplary cell fusion assay, as described above. The MCA1 hybridoma was selected for use, based on its relatively high potency in neutralization of cytotoxicity (activity at a dilution of 1:10, 912) and relatively low potency in inhibition of ADP ribosyl transferase (ART) activity.

TABLE 7

| Hybridoma of ART[2] | Neutralization of Cytotoxicity[1] | Inhibition |
| --- | --- | --- |
| MCA1 | 1:10,912 | 1:2 |
| MCA2 | 1:2048 | 1:10,912 |
| MCA3 | 1:5012 | 1:5012 |

Although preferred embodiments of the invention are described herein in detail, it will be understood by those skilled in the art that variations may be made thereto without departing from the spirit of the invention or the scope of the appended claims.

It is claimed:

1. A method of preventing infection by *Pseudomonas aeruginosa* in a subject, comprising
administering to the subject a monoclonal antibody characterized by immunoreactivity with an Exo S peptide epitope formed by the sequence SEQ ID NO: 2 (C A T T A T G P N G S C), and by immunoreactivity with a Pseudomonas pilin peptide selected from the group consisting of SEQ ID NO: 4, SEQ ID NO: 5, SEQ ID NO: 6, SEQ ID NO: 7, SEQ ID NO: 8, SEQ ID NO: 9 and SEQ ID NO: 10.

2. The method of claim 1, wherein the antibody is further characterized by ability to inhibit binding of *Pseudomonas aeruginosa* to a human epithelial cell.

3. The method of claim 1, wherein the peptide epitope has the sequence SEQ ID NO: 2 (C A T T A T G P NGSC).

* * * * *